United States Patent
Becker et al.

(10) Patent No.: US 11,922,644 B2
(45) Date of Patent: Mar. 5, 2024

(54) CALIBRATION PROCEDURES FOR HELMET BASED WELD TRACKING SYSTEMS

(71) Applicant: Illinois Tool Works Inc., Glenview, IL (US)

(72) Inventors: William Joshua Becker, Manitowoc, WI (US); Brett Sheleski, Appleton, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 261 days.

(21) Appl. No.: 17/669,787

(22) Filed: Feb. 11, 2022

(65) Prior Publication Data

US 2023/0260138 A1  Aug. 17, 2023

(51) Int. Cl.
*G06T 7/292* (2017.01)
*G01B 11/14* (2006.01)
(Continued)

(52) U.S. Cl.
CPC .............. *G06T 7/292* (2017.01); *G01B 11/14* (2013.01); *G01B 11/26* (2013.01);
(Continued)

(58) Field of Classification Search
CPC ........... G06T 7/292; G06T 7/80; G06T 7/246; G06T 7/73; G01B 11/14; G01B 11/26; G06Q 10/06398
(Continued)

(56) References Cited

U.S. PATENT DOCUMENTS 9,511,443 B2  12/2016  Pfeifer
9,522,437 B2  12/2016  Pfeifer
(Continued)

FOREIGN PATENT DOCUMENTS

EP  3268949  1/2018
EP  3318360  5/2018
(Continued)

OTHER PUBLICATIONS

Extended European Search Report Appln No. 22156358.8, dated Jul. 14, 2022, 11 pages.
(Continued)

*Primary Examiner* — Jeffery A Williams
*Assistant Examiner* — Kristin Dobbs
(74) *Attorney, Agent, or Firm* — McAndrews, Held & Malloy, Ltd.

(57) ABSTRACT

Described herein are examples of weld tracking systems implemented via a welding helmet. The welding helmet includes weld tracking sensors configured to allow the welding helmet to track a welding-type tool and/or an arc generated by the welding-type tool. The welding helmet also includes helmet tracking sensors configured to allow the welding helmet to track its own position and/or orientation relative to a reference point in the welding environment. By tracking itself as well as the welding-type tool and/or arc, the welding helmet can differentiate between its own movement, and movement of the welding-type tool and/or arc. By knowing the spatial relationship between the different sensors of the welding helmet, the tracking information can be combined and used for weld tracking. By implementing the weld tracking system in the welding helmet, the weld tracking system becomes portable and usable outside of the usual fixed confines of weld tracking systems.

20 Claims, 12 Drawing Sheets

(51) Int. Cl.
    *G01B 11/26* (2006.01)
    *G06Q 10/0639* (2023.01)
    *G06T 7/246* (2017.01)
    *G06T 7/73* (2017.01)
    *G06T 7/80* (2017.01)

(52) U.S. Cl.
    CPC ....... *G06Q 10/06398* (2013.01); *G06T 7/246* (2017.01); *G06T 7/73* (2017.01); *G06T 7/80* (2017.01); *G06T 2207/30108* (2013.01); *G06T 2207/30204* (2013.01); *G06T 2207/30244* (2013.01)

(58) Field of Classification Search
    USPC .......................................................... 348/90
    See application file for complete search history.

(56) References Cited

U.S. PATENT DOCUMENTS

| | | |
|---|---|---|
| 9,922,460 B2 | 3/2018 | Denis |
| 9,975,196 B2 | 5/2018 | Zhang et al. |
| 10,032,388 B2 | 7/2018 | Sommers et al. |
| 10,373,517 B2 | 8/2019 | Becker |
| 10,512,983 B2 | 12/2019 | Zhang |
| 10,596,650 B2 | 3/2020 | Pfeifer |
| 10,773,330 B2 | 9/2020 | Zhang |
| 2013/0206741 A1 | 8/2013 | Pfeifer et al. |
| 2016/0125594 A1 | 5/2016 | Becker |
| 2016/0207135 A1 | 7/2016 | Beeson |
| 2016/0214198 A1 | 7/2016 | Hsu |
| 2018/0126476 A1 | 5/2018 | Meess et al. |
| 2018/0130377 A1 | 5/2018 | Meess |
| 2018/0308385 A1 | 10/2018 | Sommers et al. |
| 2019/0172195 A1 | 6/2019 | Becker et al. |
| 2020/0374510 A1 | 11/2020 | Berends |
| 2022/0031515 A1 | 2/2022 | Becker |
| 2022/0258268 A1 | 8/2022 | Becker |

FOREIGN PATENT DOCUMENTS

| | | | |
|---|---|---|---|
| EP | 3789151 A1 * | 3/2021 | ........... B23K 9/0953 |
| EP | 4044155 | 8/2022 | |
| WO | 2005102230 | 11/2005 | |
| WO | 2013119749 | 8/2013 | |

OTHER PUBLICATIONS

Murauer et al.; A Task-Independent Design and Development Process for Cognitive Products in Industrial Applications, PETRA'19, Jun. 5-7, 2019, Rhodes, Greece, 10 pages.

European Office Communication Appln No. 22156369.5 dated Aug. 22, 2022, 2 pages.

European Patent Office, Search Report, Application No. 23153203.7, dated Aug. 7, 2023, 8 pages.

White et al;, Low-cost simulated MIG welding for advancement in technical training, Virtual Reality, Springer-Verlag, LO, vol. 15, No. 1, May 21, 2010, pp. 69-81.

Apple; Understanding ARKit Tracking and Detection, https://developer.apple.com/videos/play/wwdc2018/610/, 2022, 2 pages.

Aiteanu; Virtual and Augmented Reality Supervisor for a New Welding Helmet, Feb. 2005, 150 pages.

* cited by examiner

CALIBRATION PROCEDURES FOR HELMET BASED WELD TRACKING SYSTEMS

TECHNICAL FIELD

The present disclosure generally relates to weld tracking systems, and, more particularly, to calibration procedures for helmet based weld tracking systems.

BACKGROUND

Weld tracking refers to the practice of tracking how, when, and where a welding-type operation occurs. Weld tracking systems are used to automate as much of the practice as possible. The data captured by weld tracking systems can be used for quality assurance, operator training, and/or analytics.

Limitations and disadvantages of conventional and traditional approaches will become apparent to one of skill in the art, through comparison of such systems with the present disclosure as set forth in the remainder of the present application with reference to the drawings.

BRIEF SUMMARY

The present disclosure is directed to calibration procedures for helmet based weld tracking systems, substantially as illustrated by and/or described in connection with at least one of the figures, and as set forth more completely in the claims.

These and other advantages, aspects and novel features of the present disclosure, as well as details of an illustrated example thereof, will be more fully understood from the following description and drawings.

BRIEF DESCRIPTION OF THE DRAWINGS

The figures are not necessarily to scale. Where appropriate, the same or similar reference numerals are used in the figures to refer to similar or identical elements.

DETAILED DESCRIPTION

Figure 1:
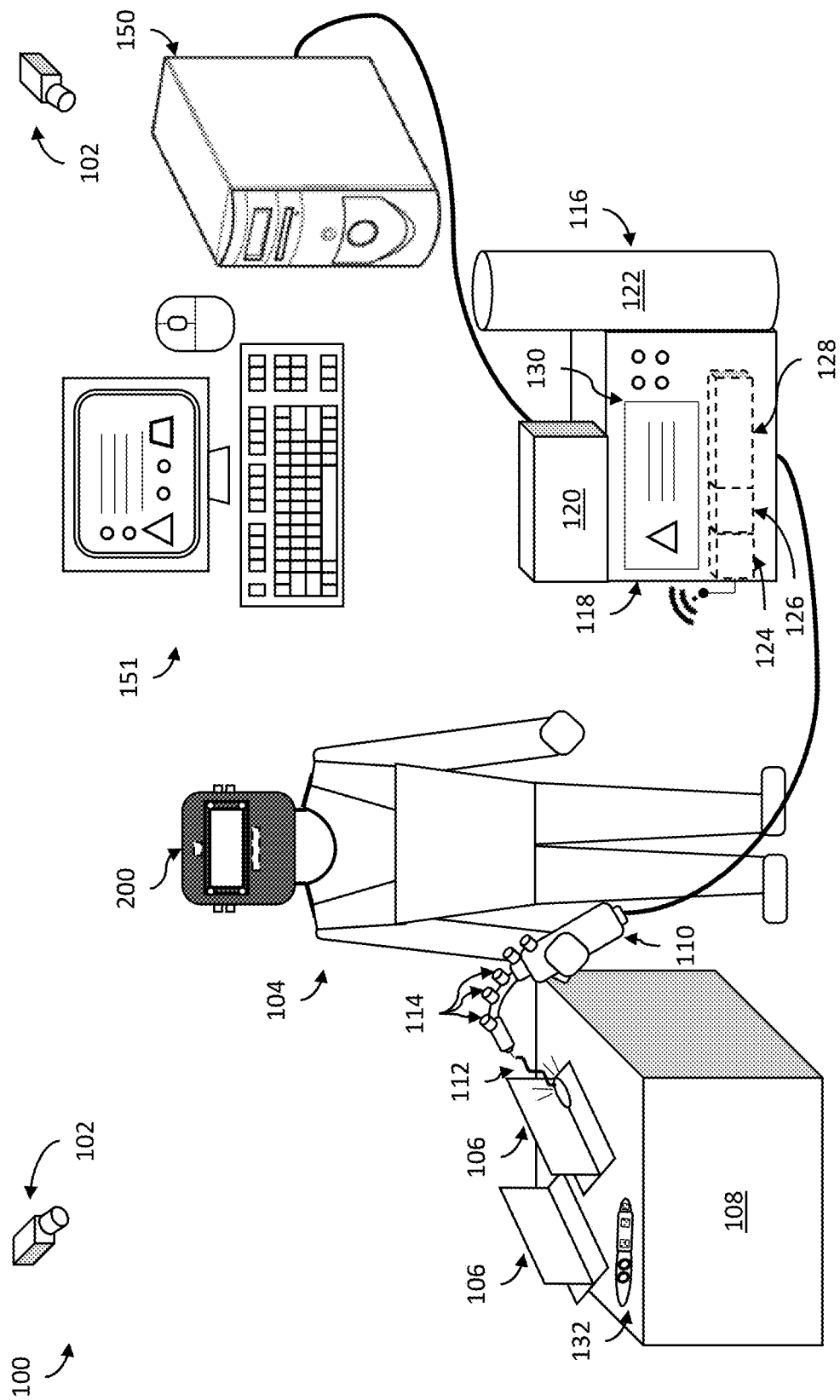
FIG. 1 shows an example of a weld tracking system, in accordance with aspects of this disclosure.

Some examples of the present disclosure relate to weld tracking systems that may be implemented entirely in (and/or on) a welding helmet. In some examples, having such a helmet based weld tracking system may provide a convenient, compact, and portable means of weld tracking, that is not restricted to the confines of a fixed weld tracking system.

In some examples, a helmet based weld tracking system may track its own position and/or orientation relative to a reference point in a welding environment, as well as the position and/or orientation of a welding-type tool and/or arc relative to the helmet. In this way, the helmet based weld tracking system can differentiate between movement of the helmet and movement of the tool and/or arc. By tracking movement of the tool and/or arc the weld tracking system can analyze the welding technique of an operator, the location(s) of the welding operation(s), and/or the sequence of welding operations. In cases where the weld tracking data, welding technique, welding location, and/or weld sequence deviates from what is expected, the helmet based weld tracking systems may offer corrective feedback, change welding parameters to compensate, and/or disable welding entirely. In some examples, the weld tracking system may be calibrated to enable helmet based weld tracking.

Some examples of the present disclosure relate to a non-transitory computer readable medium comprising machine readable instructions which, when executed by a processor, cause the processor to: identify an initial first position of a first sensor system relative to a reference point based on initial first sensor data captured by the first sensor system; identify an initial second position of a second sensor system relative to a stationary trackable object based on initial second sensor data captured by the second sensor system, the first sensor system being in a fixed spatial relationship relative to the second sensor system, the first and second sensor systems comprising a helmet sensor system; determine, after a first duration of movement of the helmet sensor system, a subsequent first position of the first sensor system relative to the reference point based on subsequent first sensor data captured by the first sensor system, determine, after the first duration of movement of the helmet sensor system, a subsequent second position of the second sensor system relative to the trackable object based on subsequent second sensor data captured by the second sensor system; and identify a vector relationship between the first sensor system and the second sensor system based on the initial first position of the first sensor system, the initial second position of the second sensor system, the subsequent first position of the first sensor system, and the subsequent second position of the second sensor system.

In some examples, the subsequent first sensor data and subsequent second sensor data are captured at approximately the same time, or captured when the helmet sensor system is stationary. In some examples, the non-transitory computer readable medium further comprises machine readable instructions which, when executed by the processor, cause the processor to record the vector relationship in the non-transitory computer readable medium or a separate memory. In some examples, the trackable object is a welding-type tool, a marker, or a rigid body configuration of markers.

In some examples, the non-transitory computer readable medium further comprises machine readable instructions which, when executed by the processor, cause the processor to: identify an initial first orientation of the first sensor system relative to the reference point based on the initial first sensor data captured by the first sensor system; identify an initial second orientation of the second sensor system relative to the stationary trackable object based on the initial second sensor data captured by the second sensor system; determine, after the first duration of movement of the helmet sensor system, a subsequent first orientation of the first sensor system relative to the reference point based on the subsequent first sensor data captured by the first sensor system; and determine, after the first duration of movement of the helmet sensor system, a subsequent second orientation of the second sensor system relative to the trackable object based on the subsequent second sensor data captured by the second sensor system, wherein the vector relationship between the first sensor system and the second sensor system is further identified based on the initial first orientation of the first sensor system, the initial second orientation of the second sensor system, the subsequent first orientation of the first sensor system, and the subsequent second orientation of the second sensor system.

In some examples, the non-transitory computer readable medium further comprises machine readable instructions which, when executed by the processor, cause the processor to: capture, after, or between, a plurality of additional movements of the helmet sensor system, additional first sensor data and additional second sensor data via the first sensor system and second sensor system, respectively; determine additional first positions of the first sensor system relative to the reference point based on the additional first sensor data captured by the first sensor system; and determine additional second positions of the second sensor system relative to the trackable object based on the additional second sensor data captured by the second sensor system, wherein the vector relationship between the first sensor system and the second sensor system is further determined based on the additional first positions of the first sensor system, and the additional second positions of the second sensor system.

In some examples, the non-transitory computer readable medium further comprises machine readable instructions which, when executed by the processor, cause the processor to: monitor, via the first sensor system, when the first sensor system is retained by a welding helmet, a helmet position and a helmet orientation of the welding helmet relative to a second reference point in a welding environment; track, via the second sensor system, when the second sensor system is retained by the welding helmet, a position or orientation of the welding-type tool, or of an arc produced by the welding-type tool, relative to the second sensor system; and determine a welding position or welding orientation of the welding-type tool, or the arc, relative to the reference point based on the helmet position and the helmet orientation relative to the reference point, the position or orientation of the welding-type tool, or the arc, relative to the second sensor system, and the vector relationship between the first sensor system and second sensor system.

Some examples of the present disclosure relate to a method of determining a vector relationship between a first sensor system and a second sensor system of a welding helmet, the method comprising: determining, via processing circuitry, an initial first position and an initial first orientation of a first sensor system relative to a reference point based on initial first sensor data captured by the first sensor system; determining, via the processing circuitry, an initial second position and an initial second orientation of a second sensor system relative to a stationary trackable object based on initial second sensor data captured by the second sensor system, the first sensor system being in a fixed spatial relationship relative to the second sensor system, the first and second sensor systems comprising a helmet sensor system; after a first duration of movement of the helmet sensor system, determining, via the processing circuitry, a subsequent first position and a subsequent first orientation of the first sensor system relative to the reference point based on subsequent first sensor data captured by the first sensor system, after the first duration of movement of the helmet sensor system, determining, via the processing circuitry, a subsequent second position and a subsequent second orientation of the second sensor system relative to the trackable object based on subsequent second sensor data captured by the second sensor system; and determining, via the processing circuitry, the vector relationship between the first sensor system and the second sensor system based on the initial first position of the first sensor system, the initial first orientation of the first sensor system, the initial second position of the second sensor system, the initial second orientation of the second sensor system, the subsequent first position of the first sensor system, the subsequent first orientation of the first sensor system, the subsequent second position of the second sensor system, and the subsequent second orientation of the second sensor system.

In some examples, the method further comprises executing the first duration of movement of the helmet sensor system via a movement system. In some examples, the first duration of movement is executed while keeping the trackable object in a field of view of the second sensor system. In some examples, the method further comprises recording the vector relationship in memory circuitry of the welding helmet, wherein the vector relationship is associated with a timestamp when recorded in memory circuitry. In some examples, the trackable object is a welding-type tool, a marker, or a rigid body configuration of markers.

In some examples, the method further comprises after, or between, a plurality of additional movements of the helmet sensor system, capturing additional first sensor data and additional second sensor data via the first sensor system and second sensor system, respectively; determining, via the processing circuitry, additional first positions and additional first orientations of the first sensor system relative to the reference point based on the additional first sensor data captured by the first sensor system; and determining, via the processing circuitry, additional second positions and additional second orientations of the second sensor system relative to the trackable object based on the additional second sensor data captured by the second sensor system, wherein the vector relationship between the first sensor system and the second sensor system is further determined based on the additional first positions and additional first orientations of the first sensor system, and the additional second positions and additional second orientations of the second sensor system.

In some examples, the method further comprises monitoring, via the first sensor system when the helmet sensor system is retained by the welding helmet, a helmet position and a helmet orientation of the welding helmet relative to a second reference point in a welding environment; tracking, via the second sensor system, a position or orientation of the welding-type tool, or of an arc produced by the welding-type tool, relative to the second sensor system; and determining, via control circuitry of the welding helmet, a welding position or welding orientation of the welding-type tool, or the arc, relative to the reference point based on the helmet position and the helmet orientation relative to the reference point, the position or orientation of the welding-type tool, or the arc, relative to the second sensor system, and the vector relationship between the first sensor system and second sensor system.

Some examples of the present disclosure relate to a welding system, comprising: a helmet sensor system comprising a first sensor system and a second sensor system, the first sensor system being in a fixed spatial relationship relative to the second sensor system; processing circuitry; and memory circuitry comprising machine readable instructions which, when executed by the processing circuitry, cause the processing circuitry to: identify an initial first position of the first sensor system relative to a reference point based on initial first sensor data captured by the first sensor system, identify an initial second position of the second sensor system relative to a stationary trackable object based on initial second sensor data captured by the second sensor system, determine, after a first duration of movement of the helmet sensor system, a subsequent first position of the first sensor system relative to the reference point based on subsequent first sensor data captured by the first sensor system, determine, after the first duration of movement of the helmet sensor system, a subsequent second position of the second sensor system relative to the trackable object based on subsequent second sensor data captured by the second sensor system, and identify a vector relationship between the first sensor system and the second sensor system based on the initial first position of the first sensor system, the initial second position of the second sensor system, the subsequent first position of the first sensor system, and the subsequent second position of the second sensor system.

In some examples, the fixed spatial relationship is identical to a fixed helmet relationship between the first sensor system and second sensor system when the first sensor system and second system are retained by a welding helmet. In some examples, the welding system further comprises the trackable object, the trackable object comprising a welding-type tool or a rigid body configuration of markers.

In some examples, the memory circuitry further comprises machine readable instructions which, when executed by the processor, cause the processor to: identify an initial first orientation of the first sensor system relative to the reference point based on the initial first sensor data captured by the first sensor system; identify an initial second orientation of the second sensor system relative to the stationary trackable object based on the initial second sensor data captured by the second sensor system; determine, after the first duration of movement of the helmet sensor system, a subsequent first orientation of the first sensor system relative to the reference point based on the subsequent first sensor data captured by the first sensor system; and determine, after the first duration of movement of the helmet sensor system, a subsequent second orientation of the second sensor system relative to the trackable object based on the subsequent second sensor data captured by the second sensor system, wherein the vector relationship between the first sensor system and the second sensor system is further identified based on the initial first orientation of the first sensor system, the initial second orientation of the second sensor system, the subsequent first orientation of the first sensor system, and the subsequent second orientation of the second sensor system.

In some examples, the memory circuitry further comprises machine readable instructions which, when executed by the processor, cause the processor to: capture, after, or between, a plurality of additional movements of the helmet sensor system, additional first sensor data and additional second sensor data via the first sensor system and second sensor system, respectively; determine additional first positions of the first sensor system relative to the reference point based on the additional first sensor data captured by the first sensor system; and determine additional second positions of the second sensor system relative to the trackable object based on the additional second sensor data captured by the second sensor system, wherein the vector relationship between the first sensor system and the second sensor system is further determined based on the additional first positions of the first sensor system, and the additional second positions of the second sensor system.

In some examples, the memory circuitry further comprising machine readable instructions which, when executed by the processor, cause the processor to: monitor, via the first sensor system when the first sensor system is retained by the welding helmet, a helmet position and a helmet orientation of the welding helmet relative to a second reference point in a welding environment; track, via the second sensor system when the second sensor system is retained by the welding helmet, a position or orientation of the welding-type tool, or of an arc produced by the welding-type tool, relative to the second sensor system; and determine a welding position or welding orientation of the welding-type tool or the arc, relative to the reference point, based on the helmet position and the helmet orientation relative to the reference point, the position or orientation of the welding-type tool or arc relative to the second sensor system, and the vector relationship between the first sensor system and second sensor system.

FIG. 1 shows an example of a weld tracking system 100. As shown, the weld tracking system 100 includes weld tracking sensors 102 fixed within a welding environment. In some examples, the environment fixed weld tracking sensors 102 may be used to supplement and/or replace helmet based weld tracking sensors. In some examples, the weld tracking sensors 102 are configured to track a welding-type operation performed within the welding environment, such as, for example, the welding-type operation being performed by the welding operator 104 on a workpiece 106 sitting on a welding bench 108 in the example of FIG. 1.

In the example of FIG. 1, the weld tracking sensors 102 are stationary and/or mounted to fixtures (e.g., wall(s), pillar(s), ceiling, etc.). In some examples, the weld tracking sensors 102 may comprise camera sensors, optical sensors, infra-red (IR) sensors, thermal sensors, acoustic sensors, ultrasonic sensors, electromagnetic sensors, and/or other appropriate types of sensors. While two environment fixed weld tracking sensors 102 are shown in the example of FIG. 1, in some examples, more or fewer weld tracking sensors 102 may be used. In some examples, at least four environment fixed weld tracking sensors 102 may be used, placed around the environment in such a way to ensure line of sight visibility to the welding-type operation. In some examples, the weld tracking sensors 102 may include processing circuitry configured to process data captured by the weld tracking sensors 102, and/or communication circuitry configured to transmit the captured data to other components of the weld tracking system 100.

In some examples, the weld tracking sensors 102 may be configured to track the welding-type operation by tracking (and/or capturing data relating to) the position and/or orientation of a welding-type tool 110 and/or an arc 112 generated by the welding-type tool 110. In some examples, the welding-type tool 110 may be considered part of the weld tracking system 100. In the example of FIG. 1, the operator 104 is using the welding-type tool 110 to perform a welding-type operation on a workpiece 106, via the arc 112. While not shown in the example of FIG. 1 for the sake of simplicity, in some examples, the workpiece(s) 106 may be secured and/or fixed in place (e.g., relative to the welding bench 108) by a clamp and/or other welding fixture(s). In some examples, the weld tracking sensors 102 may be further configured to track (and/or capture data relating to) the workpiece(s) 106.

While depicted in FIG. 1 as a welding torch or gun configured for gas metal arc welding (GMAW), in some examples, the welding-type tool 110 may instead be a different welding-type tool 110. For example, the welding-type tool 110 may be an electrode holder (i.e., stinger) configured for shielded metal arc welding (SMAW), a torch and/or filler rod configured for gas tungsten arc welding (GTAW), a welding gun configured for flux-cored arc welding (FCAW), and/or a plasma cutter. In some examples, the welding-type tool 110 may be a mock welding-type tool, and/or be configured for mock (as opposed to live) welding-type operations, such as for (e.g., virtual/augmented reality) weld training.

In the example of FIG. 1, the welding-type tool 110 includes markers 114 attached to a handle, neck, and nozzle of the welding-type tool 110. In some examples, the markers 114 may assist the weld tracking sensors 102 and/or weld tracking system 100 in tracking the position and/or orientation of the welding-type tool 110. For example, the markers 114 may be easily recognizable by the weld tracking system 100 in (e.g., image) data captured by the weld tracking sensors 102. Thus, the markers 114 may assist in identifying and/or recognizing the welding-type tool 110.

In some examples, the markers 114 may assist in identifying and/or recognizing particular portions of the welding-type tool 110. For example, the markers 114 may define (and/or may be calibrated to define) a recognizable and/or unique geometric configuration (and/or rigid body). In some examples, this geometric configuration (and/or rigid body) can be correlated (e.g., in memory) with a known (e.g., stored in memory) structural configuration and/or model of the welding-type tool 110. Thus, by identifying and/or tracking the particular geometric configuration of markers 114, the weld tracking system 100 may be able to identify and/or track the structural configuration of the welding-type tool 110; including particular portions (e.g., nozzle, neck, handle, etc.) of the structural configuration.

In some examples, the welding-type tool 110 may include no markers 114. In such examples, the weld tracking system 100 may instead use object recognition, computer vision, and/or other image processing techniques to identify, recognize, and/or track the welding-type tool 110.

In some examples, the weld tracking system 100 may use object recognition, computer vision, and/or other image processing techniques to identify, recognize, and/or track a visually distinctive marker 114. In some examples, visually distinctive marker 114 is a marker 114 with a geometric configuration (e.g., shape, size, pattern, etc.) that appears substantially different from other elements in the welding environment (e.g., the welding-type tool 110 and/or workpiece 106). In some examples, a visually distinctive marker 114 may have an appearance that is unlikely to otherwise occur in the welding environment. In some examples, a visually distinctive marker 114 may also be asymmetrical and/or have a unique appearance at different rotational orientations, such that the rotational orientation of the marker 114 can be readily determined from the appearance of the marker 114 in an image.

FIGS. 10a-10g, depict different views of an example object 1000 that might be considered a visually distinctive marker 114 easily identifiable and/or recognizable by object recognition, computer vision, and/or other image processing techniques. As shown, the object 1000 includes a three dimensional representation of a word 1002: "Miller" (e.g., shorthand for Miller Electric). The object additionally includes a three dimensional representation of a logo 1004 (e.g., the logo of Miller Electric) that appears above the word 1002 (when viewing the word 1002 at an orientation appropriate for reading). As shown, the logo 1004 is a circle with three adjacent diagonal backslash shaped apertures. In some examples, the word 1002 and logo 1004 configuration of the object 1000 may be substantially different from other elements in the welding environment and/or unlikely to otherwise occur in the welding environment. As shown, the object 1000 is secured to a neck of the welding-type tool 110 by a connector 1006.

In the examples of FIGS. 10a-10g, the object 1000 also appears different at different rotational orientations (relative to the perspective of the viewer). For example, the perspective, top, and bottom views of the object 1000 (e.g., FIGS. 10a-10c) are easily distinguishable from one another due to the different orientations of the word 1002 and logo 1004. Additionally, the side views of the object 1000 (in FIGS. 10d and 10e) are distinguishable from each other because the object 1000 appears differently from the side when the "M" of the word 1002 is closest to viewer's perspective (e.g., FIG. 10d) than when the "r" of the word 1002 is closest to the viewer's perspective (e.g., FIG. 10e). Likewise, the front and rear views of the object 1000 (e.g., in FIGS. 10f and 10g) are distinguishable from one another because the object 1000 appears differently from the front (e.g., FIG. 10f), where the circle of the logo 1004 is closest to the viewer's perspective, than from the rear (e.g., FIG. 10g) where the lower portions of the letters of the word 1002 are closest to the viewer's perspective. These properties make the object 1000 a good example of a visually distinctive marker 114 that the weld tracking system 1000 might be able to easily identify and/or recognize using image processing techniques.

In some examples, the welding-type tool 110 may include at least three markers 114 fixed to the welding-type tool 110 relative to one another in a single plane, and a fourth marker 114 fixed to the welding-type tool 110 in a different (e.g., adjacent) plane, to define a rigid body. While a certain number of markers 114 are shown in the example of FIG. 1 attached to the handle, neck, and nozzle of the welding-type tool 110 for the purposes of illustration, in some examples more or fewer markers 114 may be attached to the handle, neck, nozzle, and/or other portions of the welding-type tool 110.

In some examples, one or more of the markers 114 may be permanently affixed to the welding-type tool 110 (e.g., via welding, molding, screws, etc.). In some examples, one or more of the markers 114 may be removably attached to the welding-type tool 110 in such a way to allow relatively easy removal and/or reattachment without the use of tools, such as, for example, through the use of adhesives, straps, hook and loop fasteners, magnets, clamps, and/or other appropriate mechanisms. In some examples, the welding-type tool 110 may include attachment features (e.g., adhesives, straps, hook and loop fasteners, magnets, etc.) configured to mate with complementary attachment features of the markers 114, to removably attach the markers 114 to the welding-type tool 110.

In some examples, one or more of the markers 114 may be passive markers 114 that require no electrical power to operate, such as, for example, reflective markers 114 and/or pattern markers 114. In some examples, one or more of the markers 114 may be active markers 114 that are electrically powered, such as, for example, IR light emitting diodes (LEDs), and/or fiducial markers (e.g., IR light sources partially covered by light blocking patterns). In some examples where the markers 114 are active markers 114, the attachment features discussed above may help to conduct electrical power to the markers 114.

In some examples where the markers 114 are active markers 114, the markers 114 may be continuously powered on, or only powered on at certain times. For example, welding-type tool 110 may include one or more sensors (e.g., inertial sensor(s), accelerometer(s), gyroscope(s), magnetic sensor(s), optical sensor(s), current/voltage sensor(s), etc.) and/or control circuitry configured to power on/off the markers 114 based on the detection(s)/measurement(s) of the sensor(s). For example, the control circuitry may be configured to turn on the markers 114 when the sensor(s) detect movement, and turn off the markers 114 after a certain period of time with no motion detected. As another example, the control circuitry may be configured to turn on the markers 114 when the sensor(s) detect a threshold amount of light (e.g., from the arc 112), a threshold amount of current/voltage being supplied to the welding-type tool 110, and/or when a welding-type operation is initiated by the welding-type tool 110 (e.g., via activation of a trigger of the welding-type tool 110). In some examples, the welding-type tool 110 may be in communication with one or more other devices of the weld tracking system 100, and may turn on/off the markers 114 based on the communication signal(s).

In some examples where one or more of the markers 114 are active markers 114, the welding-type tool 110 may include a separate power source (e.g., battery) to provide power to the marker(s) 114. In some examples, the separate power source may include one or more solar panels configured to capture light from the arc 112. In some examples where one or more of the markers 114 are active markers 114, power may be provided from mains power, and a separate power cord (not shown) may be used to route the power. In some examples where one or more of the markers 114 are active markers 114, power may be inductively supplied via welding current flowing through the welding-type tool 110. In some examples where one or more of the markers 114 are active markers 114, welding-type power supplied to the welding-type tool 110 may be used to power the markers 114.

In the example of FIG. 1, the welding-type tool 110 is connected to welding-type equipment 116 configured to provide welding-type power and/or consumables to the welding-type tool 110. In some examples, the welding-type tool 110 may transmit one or more signals to the welding-type equipment 116 (and/or other components of the weld tracking system 100) when activated, so that the welding-type equipment knows to provide welding-type power and/or consumables to the welding-type tool 110. In some examples, the welding-type equipment 116 may be considered part of the weld tracking system 100. In some examples, the welding-type equipment 116 may be omitted, or may be mock and/or simulated welding-type equipment 116, such as may be used for training, simulated, and/or mock welding-type operations.

In the example of FIG. 1, the welding-type equipment 106 comprises a welding-type power supply 118, wire feeder 120, and gas supply 122. In some examples, the wire feeder 120 may be configured to feed wire to the welding-type tool 110. In some examples, the gas supply 122 may be configured to route shielding gas to the welding-type tool 110.

In the example of FIG. 1, the power supply 118 includes power communication circuitry 124, power control circuitry 126, and power conversion circuitry 128 interconnected with one another. In some examples, the power conversion circuitry 128 may be configured to receive input power (e.g., from a generator, a battery, mains power, etc.) and convert the input power to welding-type output power, such as might be suitable for use by the welding-type tool 110 for welding-type operations. In some examples, the power control circuitry 126 may be configured to control operation of the communication circuitry 124, power conversion circuitry 128, wire feeder 120, and/or gas supply 122 (e.g. via one or more control signals) in accordance with one or more welding parameters.

In the example of FIG. 1, the welding-type equipment 116 further includes an operator interface 130. In some examples, the operator interface 130 may comprise one or more display screens, touch screens, knobs, buttons, levers, switches, microphones, speakers, lights, and/or other mechanisms through which an operator 104 may provide input to, and/or receive output from, the welding-type equipment. For example, an operator 104 may use the operator interface 130 to input one or more welding parameters (e.g., target voltage, current, wire feed speed, wire/filler type, wire/filler diameter, gas type, gas flow rate, welding-type process, material type of workpiece 106, position of welding-type process, etc.). As another example, the operator 104 may use the operator interface 130 to view and/or otherwise understand the current welding parameters of the welding-type equipment 116.

While shown as part of the power supply 118 in FIG. 1, in some examples, the operator interface 130, power control circuitry 126, and/or power communication circuitry 124 (and/or some other control/communication circuitry) may be part of the wire feeder 120 and/or gas supply 122. In some examples, the power communication circuitry 124 may be configured to facilitate communication with the welding-type tool 110 and/or a welding helmet 200 worn by the operator. In some examples, the power communication circuitry 124 may be configured to facilitate communication with a computing system 150 and/or one or more other computing systems (e.g., remote server(s)).

In the example of FIG. 1, the weld tracking system 100 further includes a computing system 150. While shown as a desktop computer in the example of FIG. 1, in some examples, the computing system 150 may instead be some other appropriate computational apparatus, such as, for example, a laptop computer, a tablet computer, and/or a web server. Though shown as being physically connected to the welding-type equipment 116 via a wire cable, in some examples, the computing system 150 may instead be in wireless communication with the welding-type equipment 116 (and/or welding helmet 200). In some examples, the computing system 150 may be implemented via the welding-type equipment 116 and/or welding helmet 200.

In some examples, the computing system 150 may implement a weld monitoring system configured to monitor, record, and/or analyze data captured and/or generated by the weld tracking system 100 and/or other weld tracking systems. For example, the computing system 150 may monitor, record, and/or analyze welding parameters of the welding-type equipment 116 during welding-type operations. As another example, the computing system 150 may monitor, record, and/or analyze information about the welding technique of the welding operator 104, location(s) of welds, and/or sequence(s) of welds during welding-type operations. In some examples, the computing system 150 may monitor, record, and/or analyze welding-type operation data for multiple welding-type operations and/or welding operators 104 when implementing the weld monitoring system. In some examples, the computing system 150 may additionally store and/or output data relating to the planned, expected, target, and/or exemplary job, work instructions, welding-type operation, welding parameters, welding location(s), weld sequence(s), and/or welding technique parameters when implementing the weld monitoring system. In some examples, the computing system 150 may be in communication with one or more other computing systems, which may additionally, or alternatively, implement the weld monitoring system.

In some examples, the computing system 150 may be configured to receive, process, and/or analyze data captured by the weld tracking sensors 102 to perform weld tracking operations. For example, the computing system 150 may analyze data received from the weld tracking sensors 102 to track the position and/or location of the welding-type tool 110, arc 112, and/or workpiece 106 in six degrees of freedom (DOF) (e.g., x, y, z coordinates and yaw, pitch, roll angles).

In some examples, the computing system 150 may determine welding technique parameters (e.g., contact to work distance, travel speed, travel angle, work angle, etc.) based on the tracked positions and/or locations of the welding-type tool 110, arc 112, and/or workpiece 106. For example, the computing system 150 may identify a position of (e.g., a nozzle of) the welding-type tool 110 and visible positions of the arc 112 closest and farthest from the (e.g., nozzle of the) welding-type tool 110, and estimate the contact to work distance as being approximately equal to the distance between the two positions (e.g., the visible length of the arc 112). As another example, the computing system 150 may identify a position of (e.g., a nozzle of) the welding-type tool 110 and a position of the workpiece 116, and estimate the contact to work distance as being approximately equal to the distance between the two positions.

In some examples, the computing system 150 may additionally, or alternatively, determine one or more welding operation parameter based on the tracked positions and/or locations of the welding-type tool 110, arc 112, and/or workpiece 106. In some examples, welding operation parameters may include welding location information (e.g., location of weld produced by arc 112 and/or welding-type operation) and/or weld sequence information (e.g., present welding location relative to ordered sequence of one or more prior welding locations). For example, the computing system 150 may identify a position of (e.g., a nozzle of) the welding-type tool 110 and positions of the arc 112 closest and farthest from the (e.g., nozzle of the) welding-type tool 110, and estimate the welding location(s) to be at the point of the arc 112 farthest from the (e.g., nozzle of the) welding-type tool 110. As another example, the computing system 150 may identify where the arc 112 intersects the workpiece 106, and estimate the welding location(s) to be at the point(s) of intersection. As another example, the computing system 150 may use both the intersection point and the farthest point from the (e.g., nozzle of the) welding-type tool 110 together to estimate the welding location(s).

In some examples, the computing system 150 may additionally, or alternatively, determine one or more welding sequences based on the determined welding location(s) and an ordered sequence of one or more prior welding locations. For example, the computing system 150 may identify the welding location of the current weld using the tracked positions and/or locations of the welding-type tool 110, arc 112, and/or workpiece 106 (as discussed above). The computing system 150 may thereafter identify the current welding location(s) as being the latest iteration in a sequence of welds that previously included an ordered sequence of one or more previous welds at one or more previously recorded welding locations. In some examples, the computing system 150 may identify an order of the sequence of welds based on timestamps associated with the one or more previously (and/or currently) recorded welding locations.

In some examples, the computing system 150 may provide feedback to a welding operator 104. For example, the computing system 150 may provide feedback as to whether their welding technique is within a threshold range of what is expected, and/or whether their technique needs to be adjusted. As another example, the computing system 150 may provide feedback as to whether the welding location is within a threshold range of what is expected, and/or needs to be adjusted. As another example, the computing system 150 may provide feedback as to whether the welding sequence is the same as what is expected, and/or needs to be adjusted. In some examples, the feedback may be provided to the operator 104 via a user interface (UI) 151 of the computing system 150 and/or the helmet I/O device(s) 208 of the welding helmet 200 (discussed further below with respect to FIGS. 2a-2b).

In the example of FIG. 1, the UI 151 of the computing system 150 includes input devices (e.g., a keyboard and mouse) as well as output devices (e.g., a display screen and speakers). In some examples, the input devices may include, for example, one or more keyboards, mice, touch screens, remote controls, and/or other suitable input devices. In some examples, the output devices may include, for example, one or more display screens, speakers, and/or other suitable output devices. In some examples, the UI 151 may include one or more (e.g., CD, DVD) drives, (e.g., USB) ports, and/or other devices through which the computing system 150 may interface with local storage devices. While not shown for the sake of simplicity and clarity, in some examples, the UI 151 is electrically connected and/or in electrical communication with the computing system 150. In some examples, the UI 151 may be considered part of the weld tracking system 100.

In the example of FIG. 1, the weld tracking system 100 further includes a calibration tool 132. In some examples, the calibration tool 132 may be used to help calibrate the weld tracking system 100 via a calibration procedure. For example, the calibration tool 132 may be used to help the weld tracking system 100 understand the 6 DOF position and/or orientation of the workpiece(s) 106 (which are typically stationary). As shown, the calibration tool 132 is a pen style pointer. In some examples, the calibration tool 132 may be differently configured. In some examples, the welding-type tool 110 may be used as the calibration tool 132.

Figure 5B:
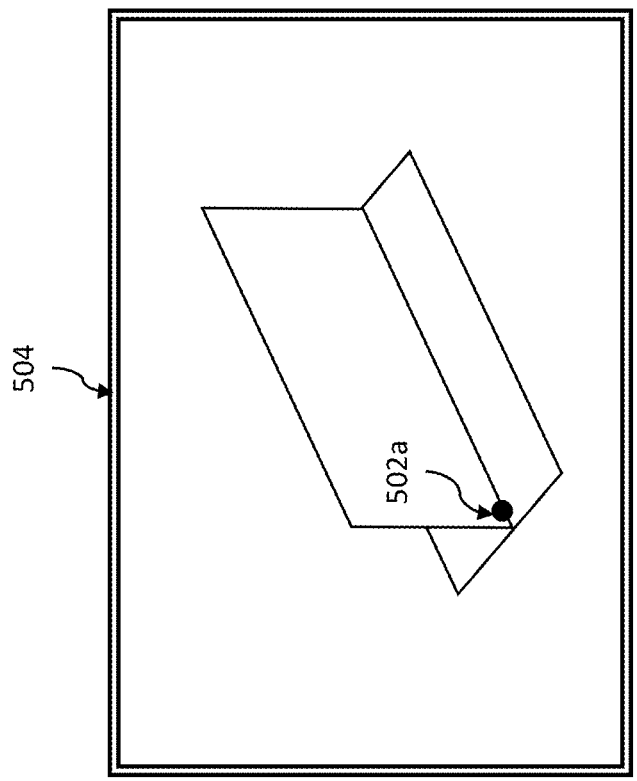
FIGS. 5a-5d show an example joint calibration process, as well as examples of how the joint may be highlighted on a display screen following the joint calibration process, in accordance with aspects of this disclosure.
Figure 5A:
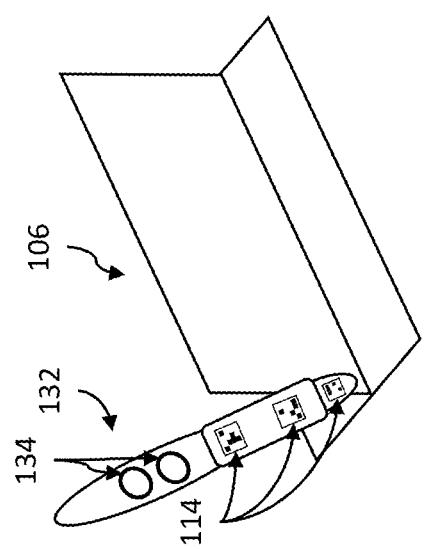

FIG. 5a shows an enlarged view of the calibration tool 132. As shown, the calibration tool 132 includes pattern markers 114 to help the weld tracking sensors 102 and/or tracking system 100 identify, recognize, and/or track the position of the calibration tool 132, (e.g., similar to that described above with respect to the welding-type tool 110). In some examples, the markers 114 may be active or passive markers 114, and/or may be powered on/off (e.g., similar to that which is described above with respect to the welding-type tool 110). In some examples, the calibration tool 132 may include no markers 114, and the weld tracking system 100 may instead use object recognition, computer vision, and/or other image processing techniques to identify, recognize, and/or track the calibration tool 132.

In the example of FIG. 5a, the calibration tool 132 further includes inputs 134. In some examples, the inputs 134 may be buttons, switches, dials, keys, knobs, and/or other appropriate user interface input mechanisms. While two inputs 134 are shown in the example of FIG. 5a, in some examples, the calibration tool 132 may include more or fewer inputs 134. In some examples, the calibration tool 132 may include communication circuitry configured to send one or more signals to the weld tracking sensors 102, welding-type equipment 116, computing system 150, welding helmet 200, and/or other components of the weld tracking system 100 when an input 134 is activated.

In the example of FIG. 1, the weld tracking system 100 further includes a welding helmet 200 worn by the welding operator 104. In some examples, the welding helmet 200 may implement portions of the weld tracking system 100, such as, for example, the weld tracking sensors 102 and/or the computing system 150. In some examples, the welding helmet 200 may comprise a convenient, compact, portable, self-contained, and/or independently operable weld tracking system unto itself. In some examples, the independence, portability, and/or capabilities of the welding helmet 200 may allow for weld tracking both without the other components of the weld tracking system 100 and/or outside of the relatively small footprint and/or range of the fixed weld tracking sensors 102.

While a welding helmet 200 may be used as a self-contained, portable, weld tracking system, in some examples, other wearable items may be also used in place of, or in addition to, a welding helmet 200. For example, a hat, vest, goggles, sleeve, wristband, collar, pendant, and/or other wearable item may be used in place of, or in addition to, a welding helmet 200 as a self-contained, portable, weld tracking system. That said, there are obvious advantages to using the welding helmet 200 as the wearable item (e.g., familiarity of operator 114, likelihood of welding-type tool 110 and/or welding-operation being visible, etc.).

Figure 2B:
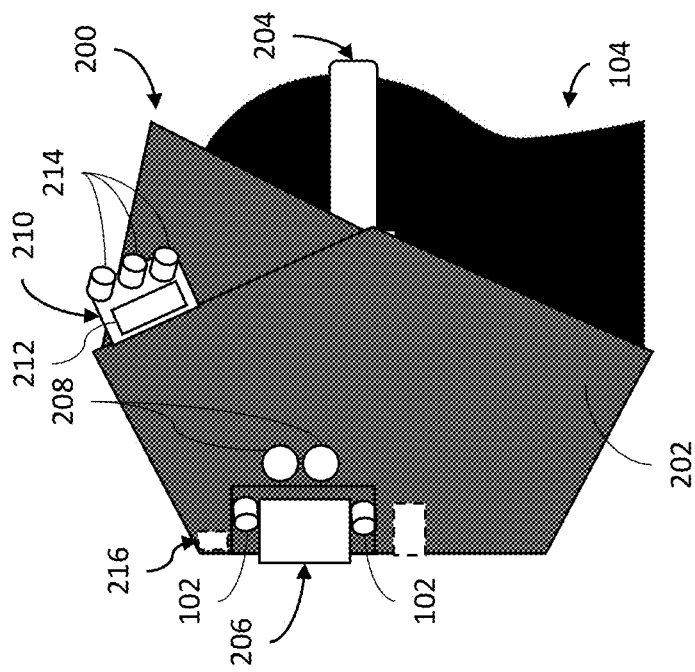
FIGS. 2a-2b show example front and side views of a welding helmet that may be used in the weld tracking system of FIG. 1, in accordance with aspects of this disclosure.
Figure 2A:
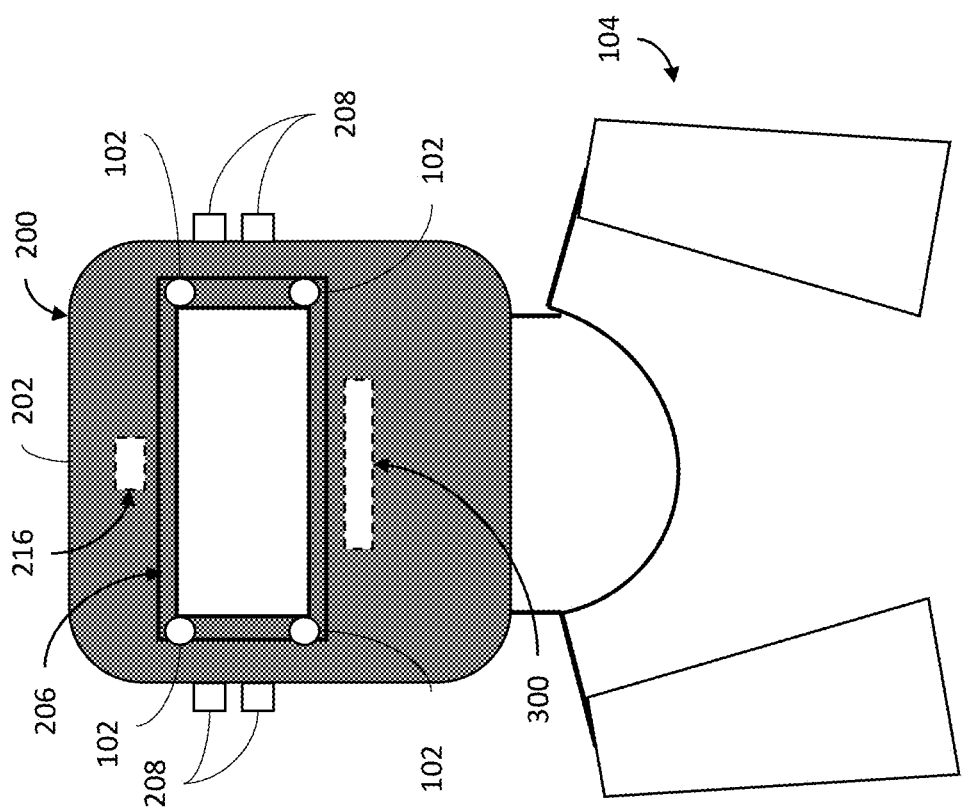

FIGS. 2a-2b show enlarged front and side view of an example welding helmet 200. As shown, the smart welding helmet 200 comprises a helmet shell 202 attached to a suspension 204. As shown, the suspension 204 comprises several straps and/or bands configured to wrap around the head of an operator 102. The straps are connected to one another and to the helmet shell 202 at least at two side attachment points on either side of the head of the operator 102. In some examples, the smart helmet 200 may be configured to rotate and/or pivot about the side attachment points to transition between raised and lowered positions. In some examples where other wearable items are used instead of, or in addition to, the welding helmet 200, the wearable items may have a retention mechanism (e.g., similar to the suspension 204) to keep the wearable securely attached to the operator 102 when worn (e.g., one or more clips, sleeves, chains, bands, pins/holders, etc.).

In the examples of FIGS. 2a-2b, the welding helmet 200 also includes a lens assembly 206 fixed to (and/or integrated into) a front portion of the helmet shell 202 at approximately eye level. In some examples, the lens assembly 206 may include a cover lens, an auto-darkening filter (ADF), and/or a display screen. In some examples, the cover lens may be (e.g., partially or fully) transparent and/or configured to allow an operator 104 to see through the cover lens and/or view the surrounding environment.

In some examples, the ADF comprises a lens (and/or lens cartridge) with a transparency that varies based on one or more signals provided by a photodiode sensor (and/or other sensor(s)). In some examples, the photodiode sensor (and/or other sensor(s)) may be configured to detect light in front of and/or around the welding helmet 200 and send one or more signals to the ADF when the detected light is above a threshold intensity (e.g., indicating the light is from the arc 112). In some examples, the signal(s) to the ADF may instead be provided by the helmet circuitry 300 (e.g., after interpreting data from the photodiode sensor and/or other sensor(s)). In this manner, when an arc 112 is present, the lens assembly 206 (and/or cover lens) may be darkened to protect the eyes of the operator 104, and when the arc 112 is not present the lens assembly 206 (and/or cover lens) may be lightened so that the operator 104 can see the surrounding welding environment. In some examples, the photodiode sensor (and/or other sensor(s)) may also be part of the welding helmet 200, lens assembly 206, and/or ADF.

In some examples, the lens assembly 206 may further include one or more display screens. In some examples, a display screen may be a near-eye display. In some examples, the display screen(s) may be semi-transparent and/or configured to overlay information (e.g., virtual/simulated/holographic objects, guidance, technique feedback, technique parameters, welding location feedback, welding location(s), welding sequence feedback, welding sequence(s), welding parameters, messages, etc.) onto at least part of cover lens (and/or lens assembly 206). In some examples, the display screen may be integrated into safety glasses attached to (and/or in communication with) the welding helmet 200.

In some examples, a display screen may cover the entire cover lens (and/or lens assembly 206). In some examples where the display screen covers the entire cover lens (and/or lens assembly 206), the ADF may be omitted. In some examples, a display screen may cover only a portion of the cover lens (and/or lens assembly 206), so as to be visible on only one side (e.g., to only one eye). In some examples, providing the display screen over both sides of the lens assembly 206 (and/or eyes) may make stereoscopic display possible, which may make it possible to display images that appear to have more depth. In some examples, a display screen may be positioned at and/or over a periphery of the lens assembly 206, so as to be less distracting.

In some examples the display screen(s) may be configured to display information about certain aspects of the welding helmet 200. For example, the display screen(s) may display settings of the ADF, tracked welding technique/operation/quality parameters, welding technique/operation/quality parameters as compared to expected parameters, welding technique/quality/operation feedback, work instructions, welding procedure specification (WPS) information, parameters of the welding equipment 116, messages, manuals, training videos/images, information about the workpiece 106, the joint about to be welded, the location of the next weld, location of the joints already welded, a virtual representation of the completed product being welded, walking directions to various locations, and/or other information. In some examples, some of this information may be received from the computing system(s) 150 and/or a weld monitoring system. In some examples, this information may be output via other helmet I/O devices 208.

In the examples of FIGS. 2a-2b, the welding helmet 200 includes helmet input/output (I/O) devices 208. In some examples, the helmet I/O devices 208 are devices through which an operator 104 may provide input to, and/or receive output from, the welding helmet 200. In some examples, the I/O devices 208 may include knobs, buttons, levers, switches, touch screens, microphones, speakers, haptic devices, lights (e.g., LEDs), and/or other appropriate I/O devices 208. In some examples, the display screen(s) may be considered part of the helmet I/O devices 208. In some examples, settings of the ADF 220 may be controlled and/or presented to the operator 102 via the helmet I/O devices 208. While shown as being retained on an external surface of the helmet shell 202 in the examples of FIGS. 2a-2b for the purposes of illustration, in some examples, some I/O devices 208 may also be retained on an internal surface of the helmet shell 202.

In the examples of FIGS. 2a-2b, the welding helmet 200 also includes weld tracking sensors 102. While four weld tracking sensors 102 are shown, in some examples, the welding helmet 200 may include more or fewer weld tracking sensors 102. In some examples, the welding helmet 200 may include at least two weld tracking sensors 102. In some examples, the weld tracking sensors 102 of the welding helmet 200 may be attached to the helmet shell 202. In some examples, the weld tracking sensors 102 of the welding helmet 200 may be part of the lens assembly 206 and/or ADF. In some examples, the weld tracking sensors 102 of the welding helmet 200 may be positioned behind and/or covered by portions of the lens assembly 206 (e.g., the cover lens) in order to protect the weld tracking sensors 102 from spatter, debris, and/or other particulates. In some examples, the weld tracking sensors 102 of the welding helmet 200 may be positioned behind the ADF, so that light from the arc 112 will be filtered through the ADF and reduced before impinging on the weld tracking sensors 102.

In some examples, the weld tracking sensors 102 of the welding helmet 200 may be fixed relative to each other and/or the helmet shell 202. In some examples, the relative positions of the weld tracking sensors 102 of the welding helmet 200 may be known, stored, entered manually, and/or automatically detected and/or derived during a calibration procedure, as discussed further below with respect to FIG. 8. As with the weld tracking sensors 102 of FIG. 1, in some examples, the weld tracking sensors 102 of the welding helmet 200 shown in FIGS. 2a-2b may comprise camera sensors, optical sensors, infra-red (IR) sensors, thermal sensors, acoustic sensors, ultrasonic sensors, and/or other appropriate types of sensors. As with the weld tracking sensors 102 of FIG. 1, in some examples, the weld tracking sensors 102 of the welding helmet 200 shown in FIGS. 2a-2b may be configured to track a welding-type operation by tracking the 6 DOF positions and/or orientations of the welding-type tool 110, arc 112, and/or workpiece(s) 106.

In the example of FIG. 2b, the welding helmet 200 additionally includes a helmet tracking system 210. In some examples, the helmet tracking system 210 may be configured to track the 6 DOF position and/or orientation of the welding helmet 200 (and/or helmet tracking system 210). In some examples, the helmet tracking system 210 may include its own control circuitry to assist in the tracking, or the helmet circuitry 300 may assist with the tracking. In some examples, it may be necessary to keep track of the position and/or orientation of the welding helmet 200 in order for the welding helmet 200 to operate as an independent weld tracking system. In the absence of the helmet tracking system 210, the welding helmet 200 might have difficulty distinguishing between movement of the welding helmet 200 and movement of the welding-type tool 110 and/or arc 112.

In some examples, the helmet tracking system 210 may be configured to track a 6 DOF position and/or orientation of the welding helmet 200 (and/or helmet tracking system 210) relative to some reference point in/of the welding environment. In some examples, the reference point may be some (e.g., stationary) object, point in space, point in a moving reference frame, and/or point in space occupied by the welding helmet 200. In some examples, one or more stationary markers 114 may be positioned at (and/or attached to) various locations around the welding environment (e.g., on the ceiling, floor, wall(s), pillar(s), furniture, fixture(s), etc.) for the helmet tracking system 210 to use as reference points.

In some examples, the reference point may be chosen at initiation, startup, and/or reset of the helmet tracking system 210. In some examples, the helmet tracking system 210 (and/or the welding helmet 200) may be configured to use a simultaneous localization and mapping (SLAM) algorithm to determine the 6 DOF position and/or orientation of the welding helmet 200 relative to the reference point. In some examples, other algorithms (e.g., time of flight) may be used.

In some examples, the helmet tracking system 210 may provide relatively reliable data during welding-type operations. However, movement of the operator 104 tends to be much less dynamic during welding-type operations. In some examples, the helmet tracking system 210 may lose track of the reference point and/or provide erroneous data if/when there is rapid movement of the welding helmet 200. In situations where there is too rapid and/or highly dynamic movement, the helmet tracking system 210 may automatically reset.

In some examples, the helmet tracking system 210 may automatically reset when a new welding-type operation begins (e.g., after some threshold period of inactivity) to ensure reliable data is gathered. In such examples, the welding helmet 200 may receive one or more signals from the welding-type tool 110 and/or welding-type equipment 116 representative of an initiation of a welding-type operation by (e.g., activation of) the welding-type tool 110. In some examples, the operator 104 may manually reset the helmet tracking system 210 (e.g., via I/O device(s) 208). In some examples, the helmet tracking system 210 (and/or welding helmet 200) may detect and/or determine the degree of movement of the welding helmet 200 and/or the corresponding reliability of the helmet tracking system 210, and inform the operator 104 (e.g., via I/O device(s) 208) so that the operator can make a decision as to whether to reset the helmet tracking system 210.

In some examples, the helmet tracking system 210 may be fixed relative to the helmet shell 202 and/or the weld tracking sensors 102 of the welding helmet 200. In some examples, the helmet tracking system 210 may be permanently affixed to the helmet shell 202 (e.g., via welding, molding, screws, etc.). In some examples, the helmet tracking system 210 removably attached to the helmet shell 202 in such a way to allow relatively easy removal and/or reattachment without the use of tools, such as, for example, through the use of adhesives, straps, hook and loop fasteners, magnets, clamps, and/or other appropriate mechanisms. In some examples, allowing for easy removability of the helmet tracking system 210 may facilitate maintenance of the helmet tracking system 210. In some examples, the helmet shell 202 may include attachment features (e.g., adhesives, straps, hook and loop fasteners, magnets, etc.) configured to mate with complementary attachment features of the helmet tracking system 210, to removably attach the helmet tracking system 210 to the helmet shell 202. In some examples, the attachment features may help to conduct electrical power from a power source 216 of the welding helmet 200 to the helmet tracking system 210.

In the example of FIG. 2b, the helmet tracking system 210 is affixed and/or attached to a rear portion of the helmet shell 202. In some examples, this may help to increase the likelihood that the reference point used by the helmet tracking system 210 is a relatively stationary point in the environment. Were the helmet tracking system 210 instead positioned on the front portion of the helmet shell 202, there would be a nontrivial risk that a dynamic and/or moving point might be referenced (e.g., like the welding-type tool 110). In some examples, the helmet tracking system 210 may instead be positioned on a side portion of the helmet shell 202, which may also increase the likelihood that the reference point used by the helmet tracking system 210 is a stationary point in the welding environment. Additionally, rear and/or side placement of the helmet tracking system 210 may help to limit interference due to the intense light, heat, and/or electromagnetic radiation given off by the arc 112.

In the example of FIG. 2b, the helmet tracking system 210 comprises a combination of sensors, including one or more inertial measurement units (IMUs) 212 (e.g., comprising one or more accelerometers, gyroscopes, and/or magnetometers) and several camera sensors 214. As shown, the camera sensors 214 are facing outward from the helmet shell 202. While three camera sensors 214 are shown in the example of FIG. 2b, in some examples, more or fewer camera sensors 214 may be used. In some examples, additional or alternative sensors may be used, such as, for example, acoustic sensors, ultrasonic sensors, IR sensors, infrared projectors/detectors, near field communication (NFC) sensors, radio frequency identification (RFID) sensors, thermal sensors, and/or other appropriate sensors. In some examples, the IMU 212, camera sensors 214, and/or other sensors may be positioned behind a casing, housing, and/or other covering to protect against spatter, debris, and/or other particulates.

In some examples, the IMU 212, camera sensors 214, and/or other sensors of the helmet tracking system 210 may capture (e.g., image and/or inertial) data relating to the position and/or orientation of the welding helmet 200 (and/or helmet tracking system 210). In some examples, this data may be analyzed to determine the position and/or orientation of the welding helmet 200 (and/or helmet tracking system 210) relative to a reference point. In some examples, the helmet tracking system 210 (and/or the welding helmet 200) may be configured to use a simultaneous localization and mapping (SLAM) algorithm to determine the 6 DOF position and/or orientation of the welding helmet 200 relative to the reference point. In some examples, the helmet tracking system 210 may include its own control circuitry to assist in the determinations. In some examples, the helmet circuitry 300 may assist with the determinations.

In some examples, the welding helmet 200 may be calibrated in order to assist with tracking the 6 DOF position and/or location of the welding helmet 200, welding-type tool 110, arc 112, and/or workpiece(s) 106. For example, the welding helmet 200 may be calibrated so that a direction of gravity is known. As another example, the welding helmet 200 may be calibrated to derive and/or determine a positional, rotational, and/or frame of reference relationship between the weld tracking sensors 102 and helmet tracking system 210 of the welding helmet 200. In some examples, the calibration may be performed automatically. In some examples, there may be a calibration procedure that may be performed at initiation and/or reset. In some examples, the welding helmet 200 may be placed in a known orientation (e.g., on a flat surface) before calibrating.

In some examples, calibration may assist the welding helmet 200 in accurately determining certain technique parameters (e.g., work angle). For example, knowing the direction of gravity may allow the welding helmet 200 to determine a plane of the welding bench 108 (e.g., perpendicular to the direction of gravity, assuming a flat bench 108), which may help to fully define an orientation of a workpiece 106 (assuming it is placed on the welding bench 108 or similar surface). In some examples, many of the technique parameters may still be accurately determined, even without the calibration.

In the examples of FIGS. 2a-2b, the welding helmet 200 further includes helmet circuitry 300 and a helmet power source 216. In some examples, the helmet circuitry 300 and helmet power source 216 may be internal to the helmet shell 202. In some examples, the helmet power source 216 may provide electrical power to the components of the welding helmet 200. In some examples, the power source 216 may comprise one or more batteries, solar panels, and/or energy harvesting devices. In some examples, one or more components of the welding helmet 200 (e.g., the helmet tracking system 210, ADF, etc.) may have a separate power source from which to draw power. In some examples, the helmet circuitry 300 may support, drive, and/or facilitate operation of the welding helmet 200.

Figure 3:
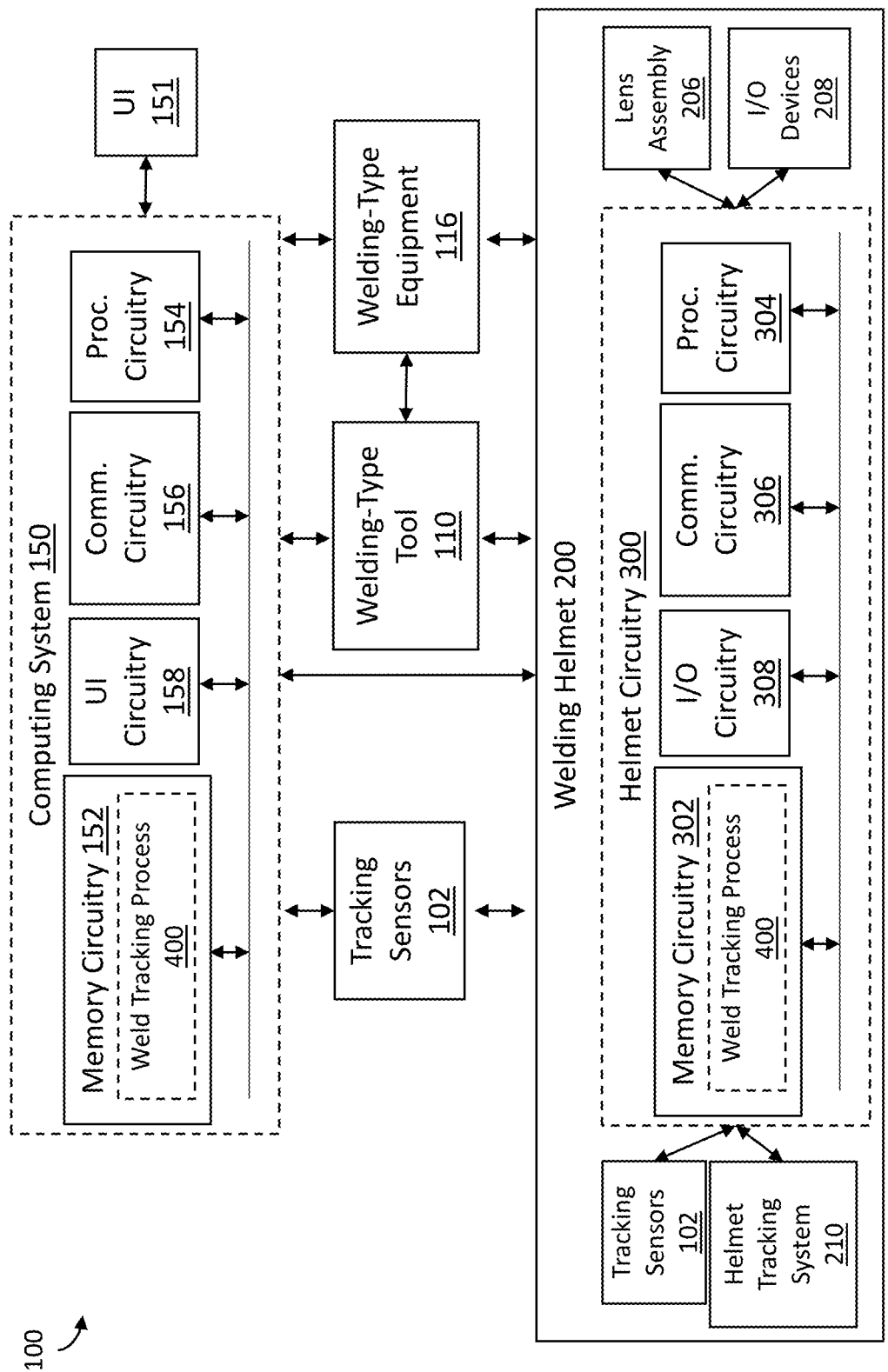
FIG. 3 is a block diagram showing example components and connections of the weld tracking system, in accordance with aspects of this disclosure.

FIG. 3 is a block diagram showing components and interconnections of the weld tracking system 100. In particular, FIG. 3 shows more detailed components of the computing system 150 and helmet circuitry 300. While not shown, the computing system 150 may further include a power source configured to provide electrical power to the computing system 150.

In the example of FIG. 3, the helmet circuitry 300 includes helmet memory circuitry 302, helmet processing circuitry 304, helmet communication circuitry 306, and helmet I/O circuitry 308 interconnected with one another via a common electrical bus. The helmet circuitry 300 is also in electrical communication with the I/O devices 208, the lens assembly 206, the weld tracking sensors 102 of the welding helmet 200, and the helmet tracking system 210.

In the example of FIG. 3, the computing system 150 includes computing memory circuitry 152, computing processing circuitry 154, computing communication circuitry 156, and computing UI circuitry 158 interconnected with one another via a common electrical bus. The computing system is also in electrical communication with the UI 151 of the computing system 150. In the example of FIG. 3, both the computing system 150 and the welding helmet 200 are in communication with the welding-type tool 110, the welding equipment 116, the fixed weld tracking sensors 102 positioned around the welding environment, and each other.

In some examples, the UI circuitry 158 and/or I/O circuitry 308 may comprise one or more drivers for the UI 151 and/or I/O devices 208, respectively. In some examples, the UI circuitry 158 and/or I/O circuitry 308 may be configured to generate one or more signals representative of input received via the UI 151 and/or I/O devices 208, respectively, and provide the signal(s) to the bus. In some examples, the UI circuitry 158 and/or I/O circuitry 308 may also be configured to control the UI 151 and/or I/O devices 208, respectively, to generate one or more outputs in response to one or more signals (e.g., received via the bus).

In some examples, the helmet communication circuitry 306 and/or computing communication circuitry 156 may include one or more wireless adapters, wireless cards, cable adapters, wire adapters, dongles, radio frequency (RF) devices, wireless communication devices, Bluetooth devices, IEEE 802.11-compliant devices, WiFi devices, cellular devices, GPS devices, Ethernet ports, network ports, lightning cable ports, cable ports, etc. In some examples, the helmet communication circuitry 306 and/or computing communication circuitry 156 may be configured to facilitate communication via one or more wired media and/or protocols (e.g., Ethernet cable(s), universal serial bus cable(s), etc.) and/or wireless mediums and/or protocols (e.g., cellular communication, general packet radio service (GPRS), near field communication (NFC), ultra high frequency radio waves (commonly known as Bluetooth), IEEE 802.11x, Zigbee, HART, LTE, Z-Wave, WirelessHD, WiGig, etc.). In some examples, the helmet communication circuitry 306 and/or computing communication circuitry 156 may be coupled to one or more antennas to facilitate wireless communication.

In some examples, the helmet communication circuitry 306 and/or computing communication circuitry 156 may be configured to facilitate communications of the computing system 150 and the welding helmet 200. In some examples, the helmet communication circuitry 306 and/or computing communication circuitry 156 may receive one or more signals (e.g., from the fixed weld tracking sensors 102, welding-type tool 110, welding-type equipment 116, etc.) decode the signal(s), and provide the decoded data to the electrical bus. As another example, the helmet communication circuitry 306 and/or computing communication circuitry 156 may receive one or more signals from the electrical bus (e.g., representative of one or more inputs received via the UI circuitry 158 and/or I/O circuitry 308) encode the signal(s), and transmit the encoded signal(s) to an external device (e.g., the weld tracking sensors 102, welding-type tool 110, welding-type equipment 116, etc.).

In some examples, the computing processing circuitry 154 and/or helmet processing circuitry 304 may comprise one or more processors, controllers, and/or graphical processing units (GPUs). In some examples, the helmet processing circuitry 304 may comprise one or more drivers for the weld tracking sensors 102 and/or helmet tracking system 210 of the welding helmet 200. In some examples, the computing processing circuitry 154 and/or helmet processing circuitry 304 may comprise counter circuitry and/or clock circuitry. In some examples, the computing processing circuitry 154 and/or helmet processing circuitry 304 may be configured to execute machine readable instructions stored in the computing memory circuitry 152 and/or helmet memory circuitry 302.

In the example of FIG. 3, the computing memory circuitry 152 and helmet memory circuitry 302 includes (and/or stores) a weld tracking process 400. The weld tracking process 400 is shown as being part of (and/or stored in) both the computing memory circuitry 152 and helmet memory circuitry 302 to show that, in some examples, either or both the computing system 150 and welding helmet 200 may perform the weld tracking process 400. In the discussion below, the general term memory is sometimes used to refer to computing memory circuitry 152 and/or helmet memory circuitry 302.

In some examples, the weld tracking process 400 may comprise machine readable instructions stored in memory and/or configured for execution by the computing processing circuitry 154 and/or helmet processing circuitry 304. In some examples, the weld tracking process 400 may be implemented via discrete circuitry (e.g., of the computing processing circuitry 154 and/or helmet processing circuitry 304) rather than, or in addition to, being part of (and/or stored in) the computing memory circuitry 152 and/or helmet memory circuitry 302.

While not shown in the example of FIG. 3, in some examples, the computing memory circuitry 152 and/or helmet memory circuitry 302 may also include (and/or store) machine readable instructions comprising counter and/or clock programs. In some examples, the computing memory circuitry 152 and/or helmet memory circuitry 302 may also include (and/or store) one or more determined, target, present, and/or past parameters (e.g., welding, welding technique, weld quality, and/or welding operation parameters). In some examples, one or more parameters may be associated with timestamp, job, project, WPS, work order, equipment, and/or other information. In some examples, the weld tracking process 400 may use and/or update one or more of the stored parameters during operation.

In some examples, the weld tracking process 400 may process data captured by weld tracking sensors 102 and track, from the captured data, the 6 DOF position and/or orientation of the welding-type tool 110, arc 112, and/or workpiece(s) 106. The weld tracking process 400 may further analyze the 6 DOF position and/or orientation of the welding-type tool 110, arc 112, and/or workpiece(s) 106, and determine certain welding technique, weld quality, and/or welding operation parameters based on the position and/or orientation data. In some examples, the weld tracking process 400 may provide feedback to an operator 104 regarding the determined welding technique, weld quality, and/or welding operation parameters, in view of one or more target and/or expected welding technique, weld quality, and/or welding operation parameters.

Figure 4:
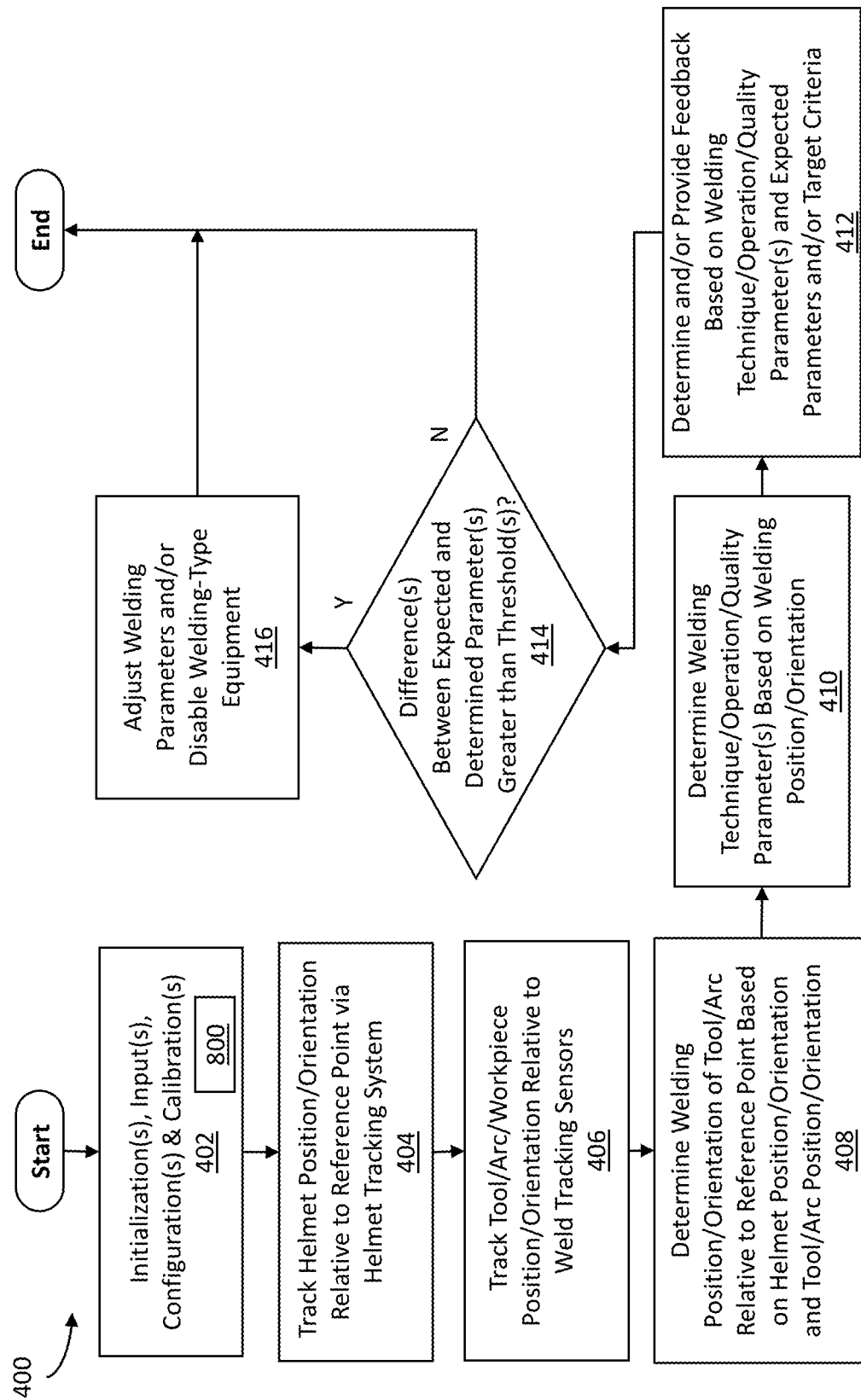
FIG. 4 is a flow diagram illustrating an example operation of a weld tracking process, in accordance with aspects of this disclosure.

FIG. 4 is a flowchart illustrating operation of an example weld tracking process 400. In the example of FIG. 4, the weld tracking process 400 begins at block 402. At block 402, the weld tracking process 400 initializes components of the weld tracking system 100 and/or the welding helmet 200. In some examples, this may include initializing the weld tracking sensors 102 fixed in the welding environment and/or secured to the welding helmet 200. In some examples, at block 402, the weld tracking process 400 may initialize the helmet tracking system 210 to select a reference point.

In some examples, at block 402, the weld tracking process 400 may receive one or more inputs from the operator 104. In some examples, the input(s) may be used to configure the weld tracking system 100 and/or weld tracking process 400. For example, the operator 104 may enter welding parameters into the welding-type equipment (e.g., via the operator interface 130). In some examples, the welding parameter(s) may be communicated to the welding helmet 200 and/or computing system 150 at block 402.

As another example, the operator 104 may enter information (e.g., via UI 151, I/O device(s) 208, etc.) relating to an upcoming welding-type operation. Information relating to the upcoming welding-type operation may include, for example, the related job, project, WPS, work order, welding location(s), welding path(s), sequenced order of welds, expected welding parameters for each weld, expected welding technique parameters for each weld, expected weld quality for each weld, and/or other pertinent information. In some examples, this information may alternatively, or additionally, be automatically loaded from memory based on some selection (e.g., of a job, project, WPS, work order, etc.), detection (e.g., a barcode, NFC device, etc.), and/or other data. In some examples, the information may be communicated to the welding helmet 200 and/or computing system 150 at block 402.

Figure 8:
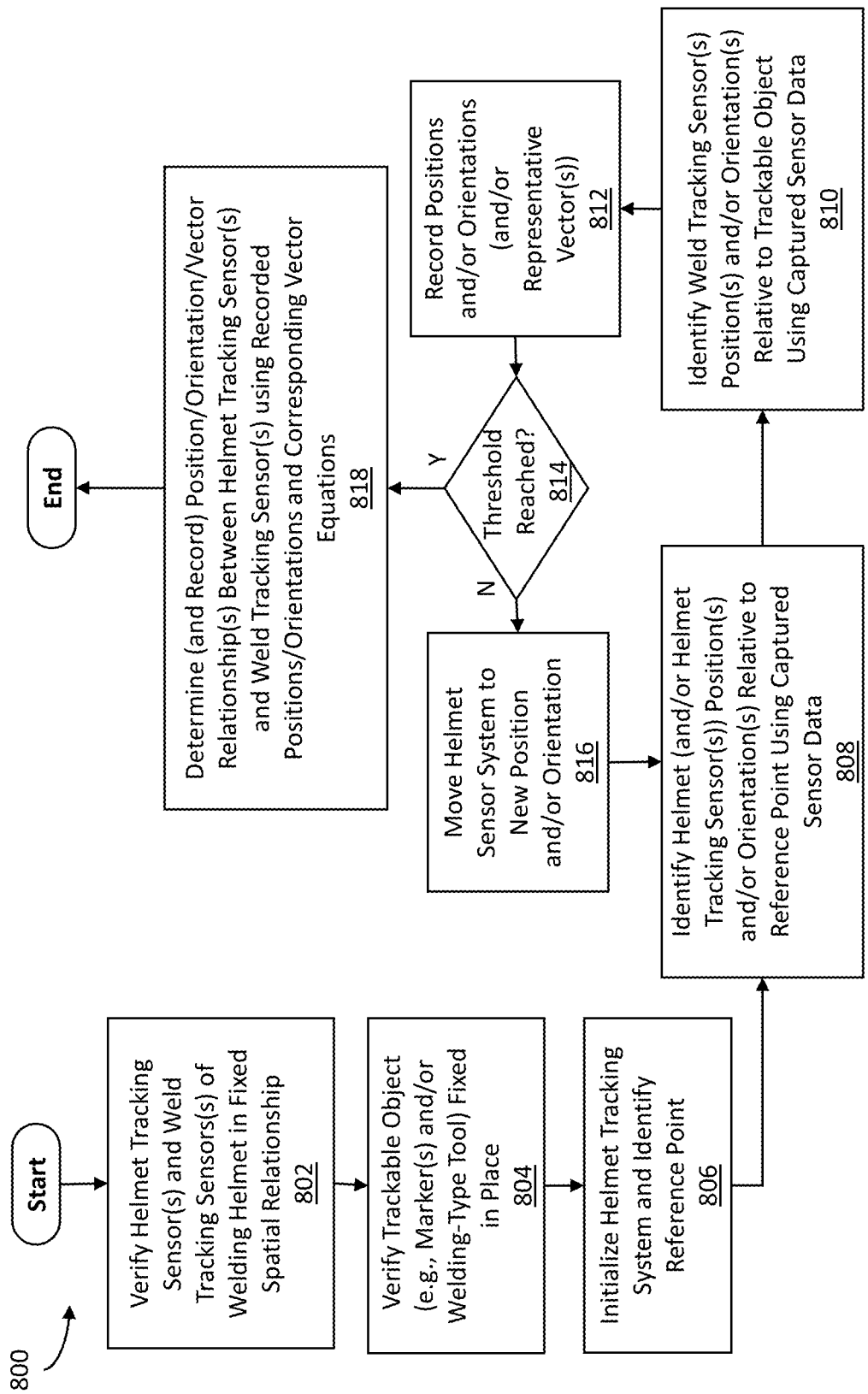
FIG. 8 is a flow diagram illustrating an example calibration procedure for determining a vector relationship between weld tracking sensors and a helmet tracking system of the welding helmet of FIG. 2a, in accordance with aspects of this disclosure.

In some examples, the weld tracking process 400 may perform and/or undergo certain calibrations at block 402. For example, the weld tracking process 400 may be calibrated to recognize the markers 114 on the welding-type tool 110, and/or correctly correlate them with a structural configuration and/or model in memory. As another example, the weld tracking process 400 may calibrate the direction of gravity for the welding helmet 200 (and/or helmet tracking system 210). As another example, the weld tracking process 400 may be calibrated with the relative locations of the weld tracking sensors 102 within the welding environment and/or on the welding helmet 200. As another example, the weld tracking process 400 may be calibrated with the relative locations of the weld tracking sensors 102 on the welding helmet 200 with respect to the helmet tracking system 210. FIG. 8, discussed below, depicts an example calibration procedure 800 that might be performed as part of block 402 to derive and/or determine a positional, rotational, and/or vector relationship between the weld tracking sensors 102 and helmet tracking system 210 of the welding helmet 200.

As another example, the weld tracking process 400 may be calibrated with the relative locations of the weld tracking sensors 102 on the welding helmet 200 with respect to the display screen(s). For example, the weld tracking process 400 may prompt the operator 104 to "touch" (e.g., with the calibration tool 132) points displayed at corners (and/or other portions) of the display screen(s). By understanding the spatial relationship(s) between the display screen(s) (e.g., showing the point(s) that are "touched") and the weld tracking sensors 102 (e.g., capturing data relating to the position/orientation of the calibration tool 132 "touching" the point(s)) the weld tracking process 400 can better display virtual feedback and/or other information relative (and/or anchored) to items in the real world.

As another example, the weld tracking process 400 may be calibrated to recognize one or more joints of a workpiece 106. This would allow the weld tracking process 400 to know the location and/or path geometry of the joint before welding begins, which may have several benefits. For example, the joint to be worked may be highlighted (e.g., via the UI 151 and/or I/O devices 208) before the welding-type operation begins. Additionally, knowledge of the joint and/or path geometry may aid in determining welding technique parameters. For example, the aim welding technique parameter may be more accurately measured with this information. Further, accurate aim technique during welding-type operations may ensure that a weld is placed in the center of the joint rather than offset to one side or the other.

In some examples, the calibration tool 132 and/or welding-type tool 110 may be used to calibrate the weld tracking process 400 to recognize the geometry of a joint of the workpiece 106. For example, the operator 104 may use the calibration tool 132 and/or welding-type tool 110 to identify endpoints (and/or intermediate points) of a joint (and/or weld path) by pointing the calibration tool 132 and/or welding-type tool 110 at the point and then activating. In some examples, there may be a particular way of activating the calibration tool 132 and/or welding-type tool 110 to indicate identification of an endpoint and/or intermediate point. For example, two or three quick, less than one or two second, activations in quick succession.

In some examples, the weld tracking process 400 may be put into a calibration mode (e.g., via input(s) 134, UI 151, operator interface 130, I/O device(s) 208, etc.) before some or all of the calibrations. This may ensure activation of the calibration tool 132 and/or welding-type tool 110 is correctly interpreted. However, in some examples, the calibration may be done in an operational mode.

In examples where calibration may be done in an operational mode, the identification of the endpoint (and/or intermediate point) may be through a short, less than one or two second, welding-type operation (e.g., a tack weld). This may be convenient, as some welding-type operations call for tack welds along and/or on opposite ends of a joint and/or weld path prior to the primary welding-type operation anyway. Further, the calibration prior to the primary welding-type operation may allow the weld tracking process 400 to highlight the joint and/or weld path to the operator 104 (e.g., via the UI 151 and/or I/O device(s) 208), which may assist the operator 104 during the welding-type operation.

In some examples, the operator 104 may calibrate the weld tracking process 400 during performance of the welding-type operation. For example, the operator 104 may identify one endpoint (e.g., using the above discussed process), and then start the welding-type operation at the opposite endpoint. In such an example, the weld tracking process 400 may conclude that the welding-type process started at the opposite endpoint, and determine the joint and/or weld path as being a line and/or the shortest path between the two endpoints (where shortest path may be a curve instead of a straight line for pipe welds and/or other curved welds).

FIGS. 5a-5d illustrate the joint and/or weld path recognition calibration of the weld tracking process 400 using the calibration tool 132 and/or welding-type tool 110. FIG. shows an example of the calibration tool 132 being used to identify a first endpoint 502a of the joint and/or weld path. In some examples, the weld tracking process 400 may capture data relating to the calibration tool 132 (e.g., via the weld tracking sensors 102), identify the position/orientation of the calibration tool 132 using the captured data, and identify the position of endpoint 502a from this data (and/or known/detected position/orientation data relating to the workpiece 106) when the calibration tool 132 is activated (e.g., via input(s) 134). FIG. 5b shows an example of how the endpoint 502a might be depicted to the operator 104 on a display screen 504 (e.g., of the UI 151, lens assembly 206, and/or I/O device(s) 208) after the calibration tool 132 is activated to perform the calibration. While the calibration tool 132 is shown being used in FIG. 5a, in some examples, the welding-type tool 110 may be used instead.

Figure 5D:
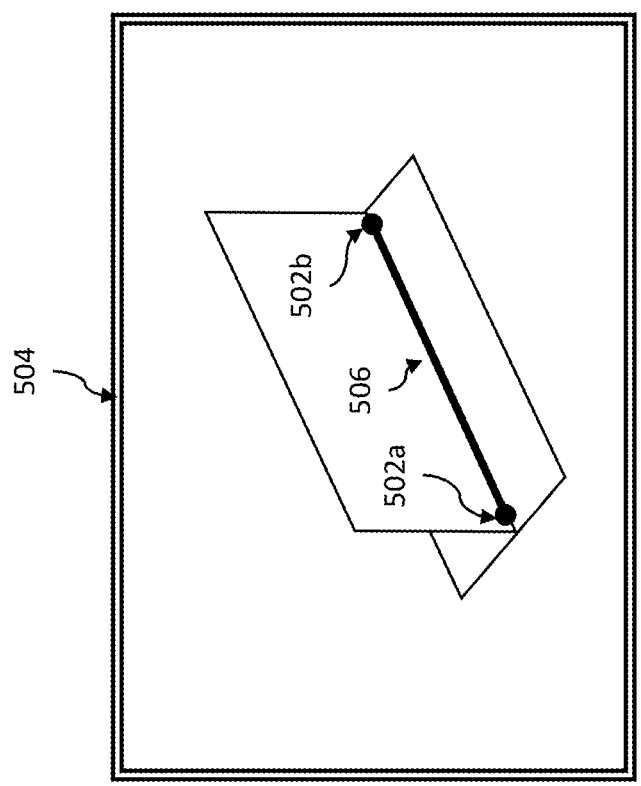
Figure 5C:
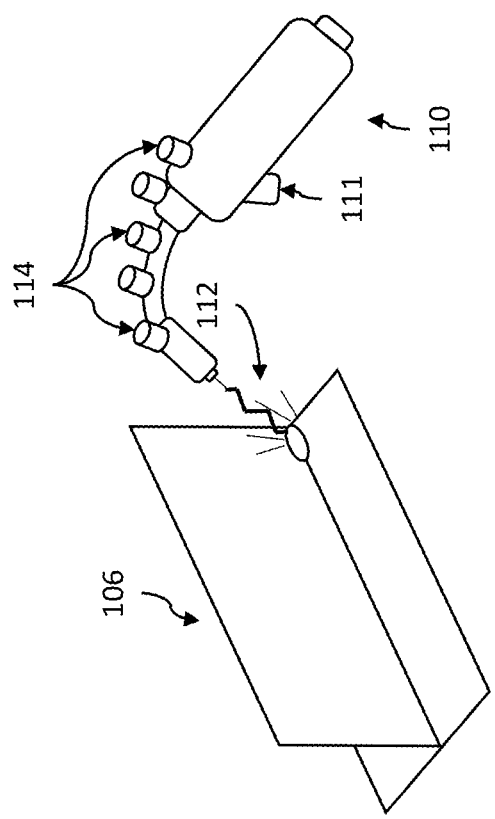

FIG. 5c shows an example of the welding-type tool 110 being used to identify a second endpoint 502 of the joint and/or weld path. As shown, the welding-type tool 110 is performing a welding-type operation (e.g., starting tack or primary welding-type operation), which generates an arc 112 and a molten pool. In some examples, the weld tracking process 400 may capture data relating to the welding-type tool 110 and/or arc 112 (e.g., via the weld tracking sensors 102), identify the position/orientation of the welding-type tool 110 and/or arc 112 based on the captured data, and identify the position of the second endpoint 502b from this data (and/or known/detected position/orientation data relating to the workpiece 106) when the welding-type operation is initiated via the welding-type tool 110 (e.g., via activation of the trigger 111). While the welding-type tool 110 is shown being used in FIG. in some examples, the calibration tool 132 may be used instead.

FIG. 5d shows an example of how the endpoints 502 and the highlight 506 connecting the endpoints 502 might be depicted to the operator 104 on the display screen 504 after both endpoints 502 are identified. In some examples, an estimated distance between endpoints 502 (e.g., as determined by the weld tracking process 400 using data captured by the weld tracking sensors 102) may also be depicted on the display screen and/or otherwise output (e.g., via I/O device(s) 208, UI 151, etc.). For example, the depiction of the distance between endpoints 502 may be shown on or adjacent the highlight 506 and/or endpoint(s) 502, or at a perimeter of the display screen.

In some examples, feedback as to whether the distance is within a threshold range of an expected distance (e.g., provided by the monitoring system) may also be provided, as well as how to correct if necessary. In some examples, feedback as to whether the position(s) of the endpoints(s) 502 (and/or connected path) are within a threshold distance of an expected position (e.g., provided by the monitoring system) may also be provided, as well as how to correct if necessary.

In some examples, the highlight 506 may be shown prior to identification of the second endpoint 502b. For example, the welding-type tool 110 (or calibration tool 132) may be used to identify the first endpoint 502a (as discussed above). Thereafter, the highlight 506 may be shown extending from the first endpoint 502a to the (e.g., nozzle) tip of the welding-type tool 110 (or calibration tool 132). Thus, as the welding-type tool 110 (or calibration tool 132) is moved away from the first endpoint 502a, the highlight 506 may be depicted as lengthening to extend between the first endpoint 502a and the moving welding-type tool 110 (or calibration tool 132).

In some examples, the second endpoint 502b may also be depicted as moving with the welding-type tool 110 (or calibration tool 132). For example, the second endpoint 502b may be shown continually positioned at (and/or anchored to) the (e.g., nozzle) tip of the welding-type tool 110 (or calibration tool 132), until the final position of the second endpoint 502b is identified. In such examples, the highlight 506 would always be depicted as extending between the endpoints 502. In some examples, an estimated distance between endpoints 502 (and/or feedback regarding the distance/position(s)) may be shown and/or continually updated as the welding-type tool 110 (or calibration tool 132) moves.

While depictions of the calibration tool 132 and welding-type tool 110 are omitted in the examples of FIGS. 5b and 5d for the sake of space and simplicity, in some examples, the calibration tool 132 and/or welding-type tool 110 may also be shown in the display screen 504. In some examples, the endpoints 502, highlight 506, and/or other feedback may be graphics overlayed on a transparent cover lens such that the operator 104 sees the endpoints 502, highlight 506, and/or other feedback superimposed on the real life workpiece 106 through the cover lens.

In some examples, the weld tracking process 400 may be calibrated to recognize the complete geometry of the workpiece(s) 106. This may allow the weld tracking process 400 to automatically identify the joints of the workpiece(s) 106 and/or intended weld paths, such as, for example, based on one or more work instructions, WPS, and/or models of the workpiece 106 stored in memory. In some examples, the calibration tool 132 and/or welding-type tool 110 may be used to identify (and/or the operator 104 may manually input) the geometry of the workpiece(s) 106. For example, the calibration tool 132 and/or welding-type tool 110 may be used to identify (and/or the operator 104 may manually input) particular points on the perimeter(s) of workpiece(s) 106, distanced from one another as much as possible. In some examples, these points may be used by the weld tracking process 400 to automatically determine a geometry of the workpiece(s) 106. In some examples, at least three points may be identified. In some examples, the points may be in different planes.

In the example of FIG. 4, the weld tracking process 400 proceeds to block 404 after block 402. At block 404, the weld tracking process 400 tracks a 6 DOF position and/or orientation of the welding helmet 200 relative to a reference point, via the helmet tracking system 210. In some examples, this may involve capturing data via the camera sensors 214 and/or IMU(s) 212 of the helmet tracking system 210, and/or analyzing the captured data determine what changes have occurred since initialization and/or reset.

In some examples, the SLAM algorithm may be used to determine the changes in position and/or orientation based on the captured data. In some examples, the SLAM algorithm may implement a continuous learning and/or training operation, whereby differences in data captured by the camera sensors 214 may be analyzed in conjunction with data captured by the IMU 212 to determine accurate movement information relative to the reference point, without the need for prior knowledge of the welding environment.

In some examples, the helmet tracking system 210 may perform all or some of the data interpretation and/or analytics, and the weld tracking process 400 may simply use the results. In some examples, the weld tracking process 400 may be involved in the data interpretation and/or analytics to determine the resulting position and/or orientation of the welding helmet 200. In some examples, the fixed weld tracking sensors 102 may also be used to help track the welding helmet 200 (e.g., via markers 114 attached to the welding helmet 200), though this may negate one of the benefits of using the welding helmet 200 as an independent mobile tracking system.

In the example of FIG. 4, the weld tracking process 400 proceeds to block 406 after block 404. At block 406, the weld tracking process 400 tracks the 6 DOF position and/or orientation of the welding-type tool 110 and/or arc 112 relative to the weld tracking sensors 102, using data captured by the weld tracking sensors 102, as discussed above. In some examples, the weld tracking sensors 102 may perform all or some of the data interpretation and/or analytics, and the weld tracking process 400 may simply use the results. In some examples, the weld tracking process 400 may analyze the data captured by the weld tracking sensors 102 to identify the positions and/or orientations of the welding-type tool 110 and/or arc 112. In some examples, the markers 114 on the welding-type tool 110 may assist in identification, recognition, and/or tracking of the welding-type tool 110 via the captured data. In some examples, data measured by sensors of the welding-type tool 110 and/or communicated to the computing system 150 and/or welding helmet 200 may also assist tracking the welding-type tool 110. In some examples, the 6 DOF position/orientation of the workpiece(s) 106 may also be tracked at block 404.

In the example of FIG. 4, the weld tracking process 400 proceeds to block 408 after block 406. At block 408, the weld tracking process 400 determines the three dimensional position and/or orientation of the welding-type tool 110 and/or arc 112 in the welding environment (and/or world space). In some examples, the three dimensional position and/or orientation of the workpiece(s) 106 may also be determined. In some examples, these determinations may be based on the prior determinations made at blocks 404 and 406. In examples where only the environment fixed weld tracking sensors 102 are used, these determinations may be relatively simple.

However, in examples where the weld tracking sensors 102 of the welding helmet 200 are used, the weld tracking process 400 may have to factor in movement and/or changes in position/orientation of the welding helmet 200 when determining the position and/or orientation of the welding-type tool 110 and/or arc 112. In such examples, the determination at block 408 may involve one or more reference frame transformations to determine the position and/or orientation of the welding-type tool 110 and/or arc 112. Such reference frame transformations may use both the position and/or orientation of the welding helmet 200 relative to the reference point, and the positions and/or orientations of the welding-type tool 110 and/or arc 112 relative to the welding helmet 200 (and/or its weld tracking sensors 102). The reference frame transformations may result in a determination of a three dimensional position and/or orientation of the welding-type tool 110 and/or arc 112 relative to the reference point (and/or in world space).

Figure 7:
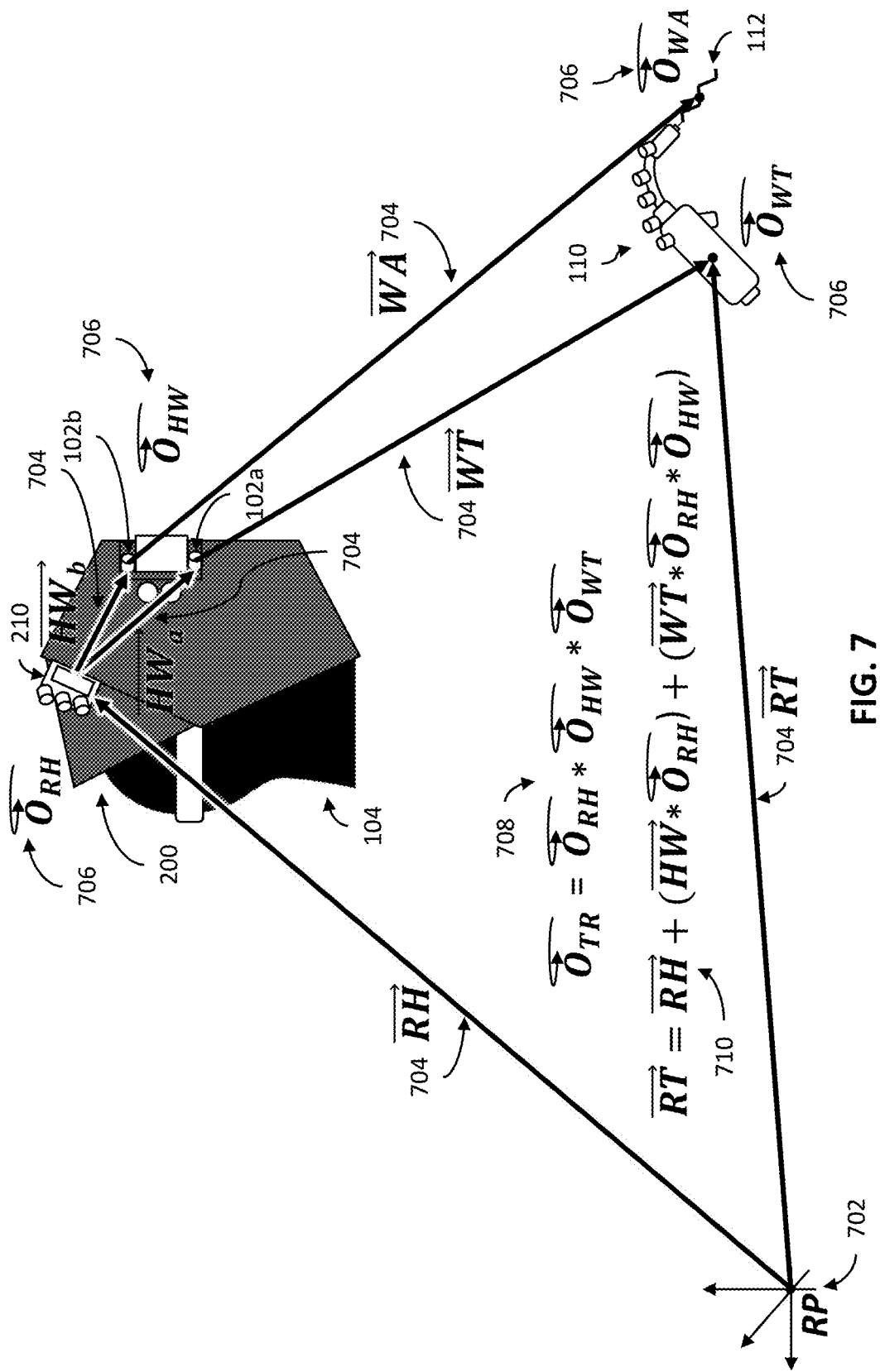
FIG. 7 shows example relationships between a reference point, a welding-type tool, and the welding helmet of FIG. 2a, in accordance with aspects of this disclosure.

FIG. 7 is a diagram depicting example position, orientation, and/or reference frame relationships between the welding helmet 200, reference point 702, welding-type tool 110, and/or arc 112. In some examples, the relationships are depicted and/or interpreted using vectors, matrices, vector mathematics, and/or matrix mathematics. In some examples, the depicted relationships may be useful in understanding how the weld tracking process 400 determines a three dimensional position and/or orientation of the welding-type tool 110 and/or arc 112 relative to a reference point (and/or in world space).

In the example of FIG. 7, a reference point 702 is shown remote from both the welding helmet 200 and welding-type tool 110. In some examples, the reference point 702 may have been selected as part of block 402 of the weld tracking process 400. In some examples, a world space frame of reference is imposed using the reference point 702, with the reference point 702 acting as an origin of a coordinate system centered about the reference point 702.

In the example of FIG. 7, a position vector 704RH is shown connecting the reference point 702 to the helmet tracking system 210 of the helmet 200. In some examples, the position vector 704RH represents a position of the helmet 200 and/or helmet tracking system 210 relative to the reference point 702.

In the example of FIG. 7, position vectors 704HWa and 704HWb are depicted connecting the helmet tracking system 210 to two weld tracking sensors 102 of the helmet 200. In some examples, the position vectors 704HW represent the position(s) of the weld tracking sensor(s) 102 relative to the helmet tracking system 210. As shown, a position vector 704WT connects a first weld tracking sensor 102a to the welding-type tool 110, and a position vector 704WA connects a second weld tracking sensor 102b to the arc 112 produced by the welding-type tool 110. In some examples, the position vector 704WT and position vector 704WA represent a position of the welding-type tool 110 and arc 112, respectively, relative to the weld tracking sensor(s) 102.

In the example of FIG. 7, an orientation vector 706 is also depicted for each of the helmet tracking system 210, weld tracking sensors 102, welding-type tool 110, and arc 112. In some examples, each orientation vector 706 is representative of an orientation (and/or rotation/angle) of an object (and/or the object's reference frame) relative to another object (and/or that object's reference frame). For example, the orientation vector $706O_{RH}$ is representative of the orientation of the helmet tracking system 210 (and/or the reference frame of the helmet tracking system 210) relative to the reference point 702 (and/or the reference frame of the reference point 702). As another example, the orientation vector $706O_{HW}$ is representative of the orientation of the weld tracking sensors 102 relative to the helmet tracking system 210. As another example, the orientation vector $706O_{WT}$ is representative of the orientation of the welding-type tool 110 relative to the weld tracking sensors 102. As another example, the orientation vector $706O_{WA}$ is representative of the orientation of the arc 112 relative to the weld tracking sensors 102.

While only one orientation vector $706O_{HW}$ is depicted for multiple weld tracking sensors 102, in some examples, each weld tracking sensor 102 may be associated with its own orientation vector 706. Likewise, in some examples, there may be separate orientation vectors $706O_{WA}$ and/or orientation vectors $706O_{WT}$ for each weld tracking sensor 102. In some examples, all the weld tracking sensors 102 may share the same orientation vectors 706.

While only two weld tracking sensors 102 and two position vectors 704HW are shown in the example of FIG. 7, in some examples, more may be used and/or applicable. Though one position vector 704WT and one position vector 704WA are each shown extending from one weld tracking sensor 102 for the sake of simplicity and clarity, in some examples a position vector 704WT and/or position vector 704WA may be considered to extend from each weld tracking sensor 102.

While the position vector 704RH and position vector 704HW are shown connecting to separate portions of the helmet tracking system 210 for the sake of clarity, in some examples, the position vectors 704 may be constructed to extend from the same point(s) (e.g., a midpoint). Though one position vector 704RH is shown for the entire helmet tracking system 210 in the example of FIG. 7, in some examples, a separate position vector 704RH may be considered to exist for each particular sensor of the helmet tracking system 210. Likewise, in some examples, separate position vectors 704HW may be considered to exist for each particular sensor of the helmet tracking system 210.

While the position vector 704WT and position vector 704RT are each shown extending to an approximate midpoint of a handle of the welding-type tool 110, in some examples the endpoint for the position vectors 704 may be considered to be at some other point of the welding-type tool 110 (e.g., at a midpoint/endpoint of the neck, nozzle, or electrode). Likewise, though the position vector 704WA is depicted extending to an approximate midpoint of the arc 112, in some examples, the position vector 704 may instead terminate at some other point along the arc 112.

In the example of FIG. 7, an orientation equation 708 is depicted. In some examples, the orientation equation 708 represents a relationship between the various orientation vectors 706 shown in FIG. 7. In particular, the orientation equation 708 indicates that the orientation vector $706O_{TR}$ (representative of the orientation of the welding-type tool 110 relative to the reference point 702) is equal to the orientation vector $706O_{RH}$ multiplied by the orientation vector $706O_{HW}$ and the orientation vector $706O_{WT}$. In other words, the orientation of the welding-type tool 110 relative to the reference point 702 ($706O_{TR}$) is equal to the combined orientations of the helmet tracking system 210 (relative to the reference point 702), weld tracking sensor(s) 102 (relative to the helmet tracking system 210), and welding-type tool 110 (relative to the weld tracking sensor(s) 102).

In some examples, the orientation equation 708 may be modified to apply to the orientation of the arc 112 rather than the orientation of the welding-type tool 110. In particular, the orientation equation 708 may be made to apply to the arc 112 by replacing the orientation vector 706$O_{TR}$ with the orientation vector 706$O_{AR}$ (representative of the orientation of the arc 112 relative to the reference point 702), and replacing the orientation vector 706$O_{WT}$ (representative of the orientation of the welding-type tool 110 relative to the weld tracking sensor(s) 102) with the orientation vector 706$O_{WA}$ (representative of the orientation of the arc 112 relative to the weld tracking sensor(s) 102).

In the example of FIG. 7, a position equation 710 is also depicted. In some examples, the position equation 710 represents a relationship between the various position vectors 704 and orientation vectors 706 shown in FIG. 7.

In particular, the position equation 710 indicates that the position vector 704RT (representative of the position of the welding-type tool 110 relative to the reference point 702) is equal to position vector 704RH (representative of the position of the helmet tracking system 210 relative to the reference point 702) plus two parenthetical vectors. The first parenthetical vector is equal to the position vector 704HW multiplied by the orientation vector 706$O_{RH}$. The second parenthetical vector is equal to the position vector 704WT multiplied by the orientation vector 706$O_{RH}$ and the orientation vector 706$O_{HW}$. In other words, the position of the welding-type tool 110 relative to the reference point 702 is equal to the position of the welding-type tool 110 relative to the weld tracking sensor(s) 102, plus the position of the weld tracking sensor(s) 102 relative to the helmet tracking system 210, plus the position of the helmet tracking system 210 relative to the reference point 702 (taking into account the relative orientations of the helmet tracking system 210 and weld tracking sensor(s) 102).

In some examples, the position equation 710 may be modified to apply to the position of the arc 112 rather than the position of the welding-type tool 110. In particular, the position equation 710 may be modified to apply to the position of the arc 112 by replacing the position vector 704RT with the position vector 704RA (not shown, but representative of the position of the arc 112 relative to the reference point 702), and replacing the position vector 704WT with the position vector 704WA.

In some examples where there are considered to be different position vectors 704 and/or orientation vectors 706 for different weld tracking sensors 102 (and/or different sensors of the helmet tracking system 210), the orientation equation 708 and/or position equation 710 may still hold true as long as the orientation vectors 706 are consistent (e.g., where orientation vector 706$O_{HW}$ and orientation vector 706$O_{WT}$ are relative to the same weld tracking sensor(s) 102), and/or the path of the position vectors 704 are interconnecting and/or continuous (e.g., where position vector 704HW and position vector 704WT both connect to the same weld tracking sensor 102). In some such examples, different implementations of the orientation equation 708 and/or position equation 710 (using different weld tracking sensors 102 and/or different sensors of the helmet tracking system 210) may yield slightly different results. In some such examples, the different results may be averaged together (and/or otherwise statistically analyzed and/or manipulated) to get a single (and/or more accurate) result.

In some examples, the weld tracking process 400 may use the position equation 710 and/or orientation equation 708 to determine a three dimensional position and/or orientation of the welding-type tool 110 and/or arc 112 relative to the reference point 702. In some examples, the weld tracking process 400 may use one or more matrices to represent and/or implement one or more orientation vectors 702 and/or position vectors 704. In some examples, the weld tracking process 400 may use one or more quaternions and/or Euler angles to represent and/or implement one or more of the orientation vectors 702 and/or position vectors 704. In some examples, the weld tracking process 400 may apply appropriate matrix mathematics to the orientation equation 708 and/or position equation 710 at block 408.

In the example of FIG. 4, the weld tracking process 400 proceeds to block 410 after block 408. At block 410, the weld tracking process 400 determines one or more welding technique and/or welding operation parameters based on the position(s) and/or orientation(s) of the welding-type tool 110 and/or arc 112 determined at block 408. In some examples, the weld tracking process 400 may also use position/orientation information about the workpiece(s) 106 and/or calibration information provided at block 402 to determine the welding technique and/or welding operation parameter(s).

In some examples, the welding technique parameters may include position/orientation, travel speed, travel direction, travel angle, work angle, contact to work distance, and/or aim of the welding-type tool 110. In some examples, the welding technique parameters may include one or more weld bead/path characteristics, such as, for example, a length, straightness, weave, whip, and/or position of the weld bead/path, and/or a distance between weld beads/paths. In some examples, data relating to the movement of the welding-type tool 110 and/or arc 112 along the entire weld path and/or joint may be evaluated to determine the weld bead/path characteristics. In some examples, other information may also be determined, such as, for example, a duration of the welding-type operation and/or a number of performed welding-type operations.

In some examples, the welding technique parameters determined by the weld tracking process 400 may depend upon certain aspects of the weld tracking process 400 and/or the weld tracking system 100. For example, the weld tracking process 400 may be able to determine more welding technique parameters when tracking just the welding-type tool 110 than when tracking just the arc 112. For instance, while it may still be possible to determine travel speed when tracking just the arc 112, it may be more difficult to track other welding technique parameters (e.g., work angle, travel angle, contact to work distance, etc.). On the other hand, it may be simpler and/or easier to track just the arc 112, while tracking the welding-type tool 110 may be a more complicated matter.

As another example, the weld tracking process 400 may be able to determine more welding technique parameters when calibrated to recognize the geometry of the workpiece(s) 106 and/or joint(s)/weld path(s) than when otherwise. In some examples, the calibration may allow the weld tracking process 400 to determine the spatial relationship(s) between the workpiece(s) 106 (and/or its joint(s)/weld path(s)) and the welding-type tool 110 and/or arc 112. In some examples, the spatial relationship(s) can be important for determining some welding technique parameters (e.g., work angle, aim, etc.). On the other hand, it may be simpler and/or easier for an operator 104 if no calibration is required.

In some examples, the contact tip to work distance welding technique parameter may be determined without calibration when tracking both the welding-type tool 110 and arc 112. For example, the weld tracking process 400 may identify the position and/or orientation of several points in space that comprise the (e.g., detectable/visible portions of) arc 112, then identify the point of the (e.g., detectable/visible) arc 112 that is farthest from the welding-type tool 110 (and/or a nozzle of the welding-type tool 110). Thereafter, the weld tracking process 400 may estimate the distance between the far point of the (e.g., detectable/visible) arc 112 and the welding-type tool 110 (and/or a nozzle of the welding-type tool 110) as being the contact tip to work distance.

As another example, the weld tracking process 400 may identify the position and/or orientation of several points in space that comprise the (e.g., detectable/visible) arc 112, then identify the points of the (e.g., detectable/visible) arc 112 that are closest to and farthest from the welding-type tool 110 (and/or a nozzle of the welding-type tool 110). Thereafter, the weld tracking process 400 may estimate the distance between the two points as being the contact tip to work distance and/or (e.g., detectable/visible) arc length. Though, in some examples, this may be a coarse and/or approximate estimate, it may still be useful. In some examples, the weld tracking system 100 may also determine contact to work distance when tracking just the welding-type tool 110, if the weld tracking system 100 has been calibrated with the geometry of the workpiece 106 and/or joint(s), by determining the distance between the welding-type tool 110 (and/or the nozzle of the welding-type tool 110) and the workpiece 106 and/or joint.

In some examples, the welding operation parameters may include welding location information and/or weld sequence information. In some examples, welding location information may include one or more (e.g., coordinate) locations of a weld produced by the arc 112 and/or the current welding-type operation. In some examples, weld sequence information may include information relating to an ordered sequence of welds produced by the operator 104 and/or welding-type tool 110 for a particular job, work order, WPS, and/or project, and/or within a threshold range of time. In some examples, the ordered sequence of welds may include the current weld produced by the arc 112 and/or the current welding-type operation. In some examples, the weld sequence information may include, for example, the relative welding locations of the current weld and/or one or more previously produced welds.

In some examples, the weld tracking process 400 may identify a position of (e.g., a nozzle of) the welding-type tool 110 and positions of the arc 112 closest and farthest from the (e.g., nozzle of the) welding-type tool 110, and estimate the welding location(s) to be at the point of the arc 112 farthest from the (e.g., nozzle of the) welding-type tool 110. In some examples, the weld tracking process 400 may identify where the arc 112 intersects the workpiece 106, and estimate the welding location(s) to be at the point(s) of intersection. As another example, the computing system 150 may use both the intersection point and the farthest point from the (e.g., nozzle of the) welding-type tool 110 together to estimate the welding location(s).

In some examples, the weld tracking process 400 may additionally, or alternatively, determine one or more weld quality parameters and/or weld defects at block 410. In some examples, the weld quality parameter and/or weld defect determination(s) may be based on the position(s) and/or orientation(s) of the welding-type tool 110 and/or arc 112 determined at block 408. In some examples, the weld quality parameter and/or weld defect determination(s) may be further based on position/orientation information about the workpiece(s) 106 and/or calibration information provided at block 402. Examples of weld quality parameters may include penetration depth, weld length, and porosity. Examples of weld defects may include cracks, undercut, excessive porosity, excessively deep/shallow penetration, burn through, lack of fusion, voids, spatter, irregular weld shape, spatter and whiskers.

In the example of FIG. 4, the weld tracking process 400 proceeds to block 412 after block 410. At block 412, the weld tracking process 400 determines feedback for, and/or provides feedback to, the operator 104. In some examples, the determination at block 412 may be based on the welding technique parameters, welding operation parameters, weld quality parameters, and/or weld defects determined at block 410, as well as certain expected weld technique parameters, welding operation parameters, weld quality parameters, and/or other target criteria. In some examples, the weld tracking process 400 may also determine and/or output other information, such as, for example, a score (e.g., numerical, grade, pass/fail, etc.), based on the determined/expected welding technique parameters, welding operation parameters, weld quality parameters, weld defects, and/or other target criteria. In some examples, the weld tracking process 400 may also output the determined/expected welding technique parameters, welding operation parameters, weld quality parameters, weld defects, and/or other target criteria.

In some examples, the expected weld technique parameters (and/or weld quality parameters) may be optimal/target values (and/or ranges of values) of the weld technique parameters (and/or weld quality parameters) in general, or for each joint, weld, and/or welding-type operation. In some examples, the target criteria may be additional optimal/target values and/or ranges of values related to the welding-type operation (e.g., location of the welding-type operation(s), duration of the welding-type operation(s), order of welding-type operations, etc.).

In some examples, the expected weld technique parameters, expected welding operation parameters, expected weld quality parameters, and/or target criteria may be determined and/or provided by a weld monitoring system. In some examples, the expected weld technique parameters, expected welding operation parameters, expected weld quality parameters, and/or target criteria may be adjusted by the operator 104 (e.g., via the UI 151 and/or I/O device(s) 208). In some examples, the expected weld technique parameters, expected welding operation parameters, expected weld quality parameters, and/or target criteria may be determined dynamically based on welding parameters of (and/or communicated from) the welding-type equipment 116.

In some examples, the expected weld technique parameters, expected welding operation parameters, expected weld quality parameters, and/or target criteria may be determined dynamically based on the position/location of the weld relative to previous weld(s) and/or within the welding environment. In some examples, other (e.g., job, work order, WPS, project, etc.) information may be determined dynamically based on the position/location of the weld relative to previous weld(s) and/or within the welding environment (i.e., the welding operation parameter(s)). In some examples, the expected weld technique parameters, expected welding operation parameters, expected weld quality parameters, and/or target criteria may be determined using sample data from expert welders. In some examples, the expected weld technique parameters, expected welding operation parameters, expected weld quality parameters, and/or target criteria may be determined based on machine learning algorithms.

In some examples, the feedback output at block 412 may be provided via the UI 151, operator interface 130, lens assembly 206, and/or I/O device(s) 208. In some examples, the feedback may be audio, visual, and/or haptic. In some examples, the weld tracking process 400 may provide feedback via the welding-type tool 110 (e.g., via one or more signals commanding a device in the welding-type tool 110 to provide visual, audio, and/or haptic output). In some examples where the feedback is visual, the feedback may be in the form of guides, arrows, lines, text, pictures, graphics, animations, videos, shapes, and/or other appropriate imagery. In some examples, feedback may be formatted with different colors, patterns, presentation styles (e.g., static, blinking, scrolling, etc.) to express different meanings. In some examples, the feedback may be displayed to one eye (monoscopic), both eyes (stereoscopic), and/or shown in peripheral portions of a display screen 504 to avoid distracting the operator 104. In some examples, the joint/weld path highlight 506 discussed above may be considered feedback. In some examples, even without the aforementioned calibration, the weld tracking process 400 may predict the joint/weld path after a welding-type operation has begun, and show a similar highlight 506 as feedback.

Figure 6:
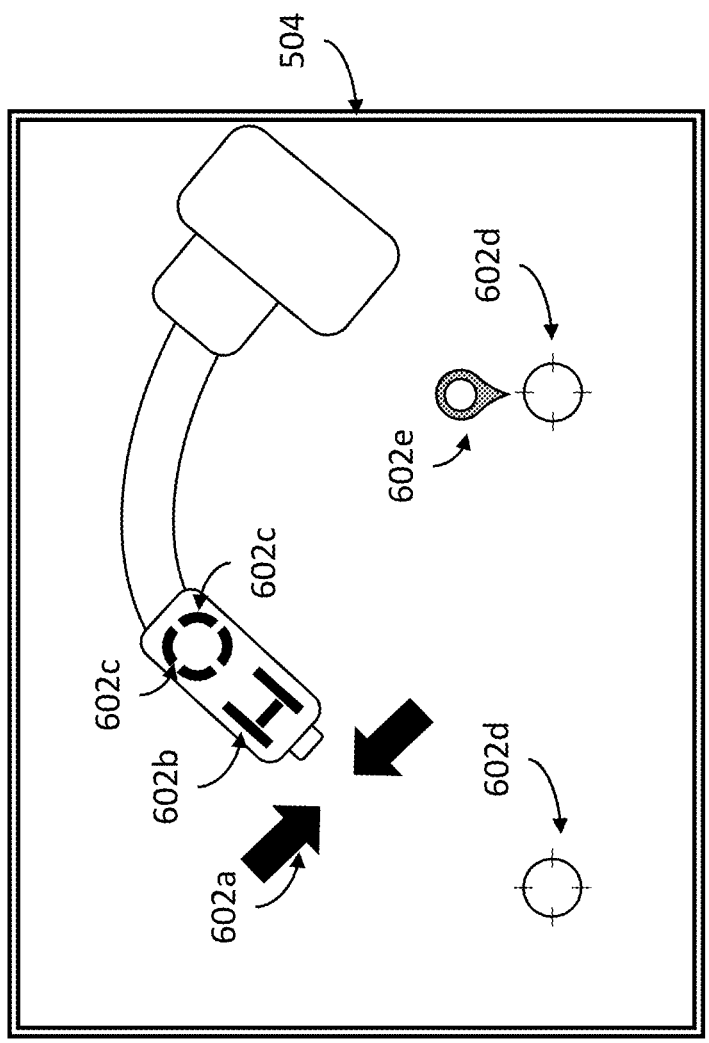
FIG. 6 shows an example of feedback presented to an operator on a display screen, in accordance with aspects of this disclosure.

FIG. 6 shows an example of how visual feedback 602 might be depicted to the operator 104 on a display screen 504 (e.g., of the UI 151, lens assembly 206, operator interface, and/or I/O device(s) 208). As shown, some of the feedback 602 is provided overlaid on a portion of the welding-type tool 110. In some examples, the welding-type tool 110 shown may be the actual welding-type tool seen through a cover lens, or a displayed representation of the real welding-type tool 110. In some examples, the feedback 602 may be shown separate from the welding-type tool 110.

In the example of FIG. 6, the feedback 602 is presented in the form of arrow feedback 602a, slider feedback 602b, arch feedback 602c, reticle feedback 602d, and marker feedback 602e. In some examples, the arrow feedback 602a may be used to provide feedback to the operator 104 regarding the travel speed of the welding-type tool 110 and/or other welding technique parameters. In some examples, the slider feedback 602b may be used to provide feedback to the operator 104 regarding the contact to tip distance of the welding-type tool 110 and/or other welding technique parameters. In some examples, the arch feedback 602c may be used to provide feedback to the operator 104 regarding the work angle and/or travel angle of the welding-type tool 110, and/or other welding technique parameters.

In some examples, the reticle feedback 602d may be used to provide feedback to the operator 104 regarding welding location(s). In the example of FIG. 6, two feedback reticles 602d are shown, indicating two different welding locations (e.g., corresponding to two different welds in an expected weld sequence). In some examples, the marker feedback 602e may be used to provide feedback to the operator 104 regarding which welding location is next in the expected weld sequence. While only one feedback marker 602e is shown in the example of FIG. 6, in some examples, multiple markers 602e may be used with different effects (e.g., colors, transparency, numbering, text etc.) to indicate whether a welding location corresponds to the next weld, a past weld, a particular number weld, and/or other information. In some examples, reticle feedback 602d may be combined with arrow feedback 602a to indicate a direction in which the operator 104 should move the welding-type tool 110 to reach the target welding location of the next weld.

In some examples, more or fewer feedback 602 may be presented. In some examples, the color, effects, and/or presentation style of the feedback may be altered to emphasize certain feedback 602 (e.g., to indicate substantial deviation of the corresponding welding technique, location, and/or sequence parameter(s) from what is expected).

In the example of FIG. 4, the weld tracking process 400 proceeds to block 414 after block 412. At block 414, the weld tracking process 400 determines whether the difference between one or more of the determined parameters and one or more of the corresponding expected parameters exceed one or more thresholds. In some examples, the thresholds may be stored in memory, received from the monitoring system, automatically determined by the weld tracking process 400 (e.g., based on the target criteria), and/or entered by the operator 104 (e.g., via the UI 151, operator interface 130, and/or I/O device(s) 208).

In the example of FIG. 4, the weld tracking process 400 ends (or, in some examples, returns to block 402 or 404) if the difference(s) are less than the threshold(s) (e.g., for all or at least a threshold number of parameters). If the difference(s) are less than the threshold(s) (e.g., for all or at least a threshold number of parameters), the weld tracking process 400 proceeds to block 416. In some examples, the weld tracking process 400 may skip block 414 and proceed to block 416 regardless.

At block 416, the weld tracking process 400 sets and/or adjusts one or more welding parameters of the welding-type equipment 116 to compensate for deviations between the expected and determined parameters. In some examples, the weld tracking process 400 may determine what settings/adjustments are appropriate (if any) and send one or more signals to the welding-type equipment 116 representative of one or more commands to adjust the welding parameter(s) to a commanded degree. Thereafter, the welding-type equipment 116 may implement the commanded settings/adjustments.

In some examples, the weld tracking process 400 may send one or more signals to the welding-type equipment 116 representative of the target criteria, determined welding technique/operation/quality parameters, expected welding technique/operation/quality parameters, and/or differences therebetween. Thereafter, the welding-type equipment 116 may itself determine what settings/adjustments (if any) are appropriate, and implement those settings/adjustments. In some examples, the welding parameters and/or values to use in the settings/adjustments may be determined based on, for example, the position/orientation of the welding-type tool 110 and/or arc 112, target criteria, determined welding technique/operation/quality parameters, expected welding technique/operation/quality parameters, and/or differences therebetween.

In some examples, the welding-type equipment 116 (and/or welding-type tool 110) may be disabled entirely if a threshold number of the parameters are above some threshold deviation. In some examples, the welding-type equipment 116 (and/or welding-type tool 110) may also be disabled if the position/orientation of the welding-type tool 110 and/or arc 112 has a position/orientation that is more than a threshold distance away from an expected welding position. In some examples, the welding-type equipment 116 (and/or welding-type tool 110) may be re-enabled if the welding-type tool 110 and/or arc 112 moves back within a threshold distance away from the expected welding position. As shown, the weld tracking process 400 ends after block 416 (though, in some examples, the weld tracking process 400 may instead return to block 402 or block 404).

FIG. 8 is a flowchart depicting an example calibration procedure 800 that might be performed by the weld tracking process 400 (e.g., as part of block 402). In some examples, the calibration procedure 800 may derive and/or determine one or more positional, rotational, reference frame, and/or vector relationships between the weld tracking sensor(s) 102 and helmet tracking system 210 of the welding helmet 200. In some examples, the weld tracking process 400 may use the relationship(s) derived/determined by the calibration procedure 800 when determining a position/orientation of the welding-type tool 110 and/or arc 112 relative to the reference point 702 (e.g., at block 408).

In the example of FIG. 8, the calibration procedure 800 begins at block 802 by verifying that the helmet tracking system 210 and helmet weld tracking sensor(s) 102 are in a fixed spatial relationship with one another. In some examples, if the positions/orientations of helmet tracking system 210 and helmet weld tracking sensor(s) 102 are not fixed with respect to one another, the derivations/determinations of the calibration procedure 800 may be difficult and/or erroneous. Thus, the calibration procedure 800 verifies that the helmet tracking system 210 and helmet weld tracking sensor(s) 102 are in a fixed spatial relationship with one another to ensure the calibration procedure 800 can correctly operate.

For example, the calibration procedure 800 may verify that the helmet tracking system 210 and helmet weld tracking sensor(s) 102 are securely attached to and/or retained by the welding helmet 200 such that their relative positions/orientations are fixed with respect to one another (even if the helmet 200 itself is moved). As another example, the calibration procedure 800 may verify that the helmet tracking system 210 and helmet weld tracking sensor(s) 102 are attached to and/or retained by a plate, bracket, holder, mount, and/or other suitable structure, such that their relative positions/orientations are fixed with respect to one another. As another example, the calibration procedure 800 may verify that the helmet tracking system 210 and helmet weld tracking sensor(s) are attached to and/or retained by a robot 906 (see, e.g., FIG. 9), and/or some other movement system, such that their relative positions/orientations are fixed relative to one another. In some examples where a non-helmet structure is used to fix the relative position(s)/orientation(s) of the helmet tracking system 210 and weld tracking sensor(s) 102, the calibration procedure 800 may additionally verify that the relative position(s)/orientation(s) are the same as when the helmet tracking system 210 and weld tracking sensor(s) 102 are attached to and/or retained by the welding helmet 200.

In some examples, the calibration procedure 800 may rely on input from the operator 104 (e.g., received via UI 151) to verify the positions/orientations of the helmet tracking system 210 and helmet weld tracking sensor(s) 102 of the welding helmet 200 are properly fixed relative to one another. In some examples, the calibration procedure 800 may query and/or prompt the operator 104 (e.g., via UI 151) to provide the verification.

In some examples, the calibration procedure 800 may use the environment fixed weld tracking sensor(s) 102 to verify that the helmet tracking system 210 and helmet weld tracking sensor(s) 102 are in a proper fixed spatial relationship with one another. For example, the calibration procedure 800 may analyze sensor data (e.g., images) captured by the environment fixed weld tracking sensor(s) 102 to verify that the helmet tracking system 210 and helmet weld tracking sensor(s) 102 are in a proper fixed spatial relationship.

In some examples, the calibration procedure 800 may additionally, or alternatively, control some corollary manufacturing, assembly, and/or fixing system to automatically fix the positions/orientations of the helmet tracking system 210 and helmet weld tracking sensor(s) 102 relative to one another. For example, the calibration procedure 800 may control a robot 906 (see, e.g., FIG. 9) to manipulate, grip, hold, and/or otherwise retain the helmet tracking system 210 and helmet weld tracking sensor(s) 102 in a proper fixed spatial relationship. In such examples, the calibration procedure 800 may be informed (and/or may detect) when the positions/orientations of the helmet tracking system 210 and helmet weld tracking sensor(s) 102 are in the proper fixed spatial relationship.

In some examples, the calibration procedure 800 may decline to proceed and/or repeat block 802 if the calibration procedure 800 cannot verify that the helmet tracking system 210 and helmet weld tracking sensor(s) 102 are in the proper fixed spatial relationship. In some such examples, the calibration procedure 800 may output one or more notifications (e.g., via UI 151) informing the operator 104 that the helmet tracking system 210 and helmet weld tracking sensor(s) 102 are not in a proper fixed spatial relationship, and/or that the calibration procedure 800 cannot proceed until this is corrected. In some such examples, the calibration procedure 800 may output instructions (e.g., via UI 151) informing the operator 104 how to put the helmet tracking system 210 and helmet weld tracking sensor(s) 102 in a fixed spatial relationship. In the description below, the term "helmet sensor system" is sometimes used as a shorthand to refer to the helmet tracking system 210 and helmet weld tracking sensor(s) 102 when they are in a fixed spatial relationship.

In the example of FIG. 8, the calibration procedure 800 proceeds from block 802 to block 804, where the calibration procedure 800 verifies that the welding-type tool 110 is fixed in place. In some examples, one or more markers 114 (e.g., that may be attached to the welding-type tool 110) may be used in place of the welding-type tool 110. In some examples, multiple markers 114 arranged as a rigid body (e.g., that may be attached to the welding-type tool 110) may be used in place of the welding-type tool 110. In some examples, the calibration procedure 800 may rely on the welding-type tool 110, marker(s) 114, and/or some other (e.g., trackable) object being fixed in the same place for during the calibration procedure 800.

In some examples, the calibration procedure 800 may rely on input from the operator 104 (e.g., received via UI 151) to verify the welding-type tool 110 (and/or other trackable object) is fixed in place. In some examples, the calibration procedure 800 may further rely on input from the operator 104 to identify the trackable object (e.g., as the welding-type tool 110, marker(s) 114, or other object). In some examples, the calibration procedure 800 may query and/or prompt the operator 104 (e.g., via UI 151) to provide the verification and/or identification.

In some examples, the calibration procedure 800 may use the environment fixed weld tracking sensor(s) 102 to verify that the welding-type tool 110 (and/or other trackable object) is fixed in place. For example, the calibration procedure 800 may analyze sensor data (e.g., images) captured by the environment fixed weld tracking sensor(s) 102 to verify that the welding-type tool 110 (and/or other trackable object) is fixed in place.

In some examples, the calibration procedure 800 may additionally, or alternatively, control some corollary attachment, fixing, and/or assembly system to automatically fix the welding-type tool 110 (and/or other trackable object) in place. For example, the calibration procedure 800 may control a robot 906 (see, e.g., FIG. 9) to manipulate, grip, hold, retain, and/or otherwise fix the welding-type tool 110 (and/or other trackable object) in place. In such examples, the calibration procedure 800 may be informed (and/or may detect) when the welding-type tool 110 (and/or other trackable object) has been fixed in place.

In some examples, the calibration procedure 800 may decline to proceed and/or repeat block 804 if the calibration procedure 800 cannot verify that the welding-type tool 110 (and/or other trackable object) is fixed in place. In some such examples, the calibration procedure 800 may output one or more notifications (e.g., via UI 151) informing the operator 104 that the welding-type tool 110 (and/or other trackable object) is not fixed in place, and/or that the calibration procedure 800 cannot proceed until this is corrected. In some such examples, the calibration procedure 800 may output instructions (e.g., via UI 151) informing the operator 104 how to fix the welding-type tool 110 (and/or other trackable object) in place.

In the example of FIG. 8, the calibration procedure 800 proceeds from block 804 to block 806, where the calibration procedure 800 initializes the helmet tracking system 210 and identifies a reference point 702. In some examples, this initialization and/or identification is similar (or identical) to the initialization and/or identification described above with respect to block 402 of the weld tracking process 400.

In the example of FIG. 8, the calibration procedure 800 proceeds from block 806 to block 808 where the calibration procedure 800 identifies the position and/or orientation of the helmet tracking system 210 relative to the reference point 702. In some examples, this identification may be based on sensor data captured by the helmet tracking system 210, similar (or identical) to that which is described above with respect to block 404 of the weld tracking process 400. In some examples, the position and/or orientation of the helmet tracking system 210 relative to the reference point 702, identified at block 808, may be represented by a positional vector 704RH and/or orientation vector 706RH, such as described above with respect to FIG. 7 (see also FIG. 9).

In the example of FIG. 8, the calibration procedure 800 proceeds from block 808 to block 810, where the calibration procedure 800 identifies the position and/or orientation of the tracked object (e.g., welding-type tool 110 and/or marker(s) 114) relative to the weld tracking sensor(s) 102. In some examples, this identification may be based on sensor data captured by the weld tracking sensor(s) 102, similar (or identical) to that which is described above with respect to block 406 of the weld tracking process 400. In some examples, the position and/or orientation of the trackable object (e.g., welding-type tool 110 and/or marker(s) 114) relative to the weld tracking sensor(s) 102 may be represented by a positional vector 704WT and/or orientation vector 706WT, such as described above with respect to FIG. 7 (see also FIG. 9).

In the example of FIG. 8, the calibration procedure 800 proceeds from block 810 to block 812 where the calibration procedure 800 records in memory the position/orientation (and/or representative vector 704/706) data identified at blocks 808 and 810. In the example of FIG. 8, the calibration procedure 800 proceeds from block 812 to block 814, where the calibration procedure 800 determines whether the calibration procedure 800 has collected enough position/orientation data to operate successfully.

In some examples, the calibration procedure 800 may require identification of a threshold number (and/or amount) of unique positions/orientations (and/or representative vectors 704/706) of the helmet sensor system for operation of the calibration procedure 800. Thus, the calibration procedure 800 may require repetition of blocks 808-812 a threshold number of times, in order to ensure the calibration procedure 800 can work effectively. In some examples, this threshold number may be six or more. In some examples, this threshold number may be twenty or more. In some examples, the threshold number may be dynamically determined, stored in memory, and/or set by the operator 104 (e.g., via UI 151).

In the example of FIG. 8, the calibration procedure 800 proceeds from block 814 to block 816 if the calibration procedure determines the threshold number has yet to be reached. At block 816, the calibration procedure 800 moves the helmet sensor system to a new position/orientation. As shown, following the movement at block 816, the calibration procedure 800 repeats blocks 808-814 to identify and/or record new relative positions/orientations (and/or representative vectors 704/706) of the helmet sensor system at the new position/orientation.

In some examples, the calibration procedure 800 may use a robot 906 (e.g., shown in FIG. 9) to move the helmet sensor system. In some examples, the calibration procedure 800 may use a different movement system to move the helmet sensor system, such as, for example, a system of one or more conveyors, cranes, gantries, swings, and/or other appropriate systems. In some examples, the movement may include a translational and/or rotational movement. In some examples, the movement may involve in one, two, and/or three of the relevant translational and/or rotational axes (e.g., x, y, z, yaw, pitch, roll). In some examples, the calibration procedure 800 may ensure that the trackable object and/or reference point 702 is still detectable by (e.g., within a field of view of) the weld tracking sensor(s) 102 and/or helmet tracking system 210, respectively, during and/or after movement.

In some examples, the calibration procedure 800 may not move the helmet sensor system. In some such examples, the calibration procedure 800 may instead rely on the operator 104 and/or some external system(s) to move the helmet sensor system. In some such examples, the calibration procedure 800 may simply verify that the helmet sensor system has been moved.

In some examples, the calibration procedure 800 may rely on input from the operator 104 (e.g., received via UI 151) to verify that the helmet sensor system has been moved. In some examples, the calibration procedure 800 may query and/or prompt the operator 104 (e.g., via UI 151) to provide the verification.

In some examples, the calibration procedure 800 may use the environment fixed weld tracking sensor(s) 102 to verify that the helmet sensor system has been moved. For example, the calibration procedure 800 may analyze sensor data (e.g., images) captured by the environment fixed weld tracking sensor(s) 102 to verify that the helmet sensor system has been moved. As another example, the calibration procedure 800 may analyze sensor data (e.g., images) captured by the helmet weld tracking sensor(s) 102 to verify that the helmet sensor system has been moved (e.g., by comparing captured sensor data (e.g., image(s)) from before and after the alleged movement).

In some examples, the calibration procedure 800 may also ensure and/or verify that the movement results in a different position and/or orientation of the helmet sensor system than previously. For example, the calibration procedure 800 may keep track (e.g., in memory) of the prior position(s)/orientation(s) (and/or associated sensor data) and verify that the new position/orientation (and/or associated sensor data) is different. In some examples, this may ensure that a variety of different sample data is collected, which can be helpful to the calibration procedure 800.

In some examples, the calibration procedure 800 may decline to proceed and/or repeat block 816 if the calibration procedure 800 cannot verify that the helmet sensor system has been properly moved. In some such examples, the calibration procedure 800 may output one or more notifications (e.g., via UI 151) informing the operator 104 that the helmet sensor system has not been properly moved, and/or that the calibration procedure 800 cannot proceed until this is corrected. In some such examples, the calibration procedure 800 may output instructions (e.g., via UI 151) informing the operator 104 how to properly move the helmet sensor system.

Notably, movement of the helmet sensor system (i.e., the helmet tracking system 210 and helmet weld tracking sensor(s) 102 when fixed relative to one another) does not change the position/orientation of the helmet tracking system 210 and helmet weld tracking sensor(s) 102 with respect to one another. This feature plays an important role in the later derivation of the positional/orientational relationship between the helmet tracking system 210 and helmet weld tracking sensor(s) 102. It is also one of the reasons the calibration procedure 800 verifies the helmet tracking system 210 and helmet weld tracking sensor(s) 102 are fixed relative to one another at block 802. It is similarly notable that the trackable object (e.g., welding-type tool 110 and/or marker(s) 114) and reference point 702 also do not move during the movement at block 816.

In some examples, sensor data is collected during (e.g., the second and/or subsequent iteration(s) of) blocks 808-810 when the helmet sensor system is substantially stationary (as opposed to being moved). This ensures that the sensor data collected by the helmet tracking system 210 at block 808 correctly correlates with the sensor data collected by the weld tracking sensor(s) 102 at block 810.

If, instead, sensor data is collected while the helmet sensor system is being moved, there is a risk that the helmet tracking system 210 and helmet weld tracking sensor(s) 102 will each collect their own sensor data at different positions/orientations of the helmet sensor system. This uncoordinated data collection can lead to uncoordinated position/orientation identifications, and subsequent errors in the calibration procedure 800.

To the extent the sensor data is collected during movement, the data collection may be synchronized such that both the helmet tracking system 210 and weld tracking sensor(s) 102 capture sensor data at approximately the same time (e.g., within a tenth of second). In some examples where data is constantly captured by the helmet tracking system 210 and/or weld tracking sensor(s) 102, the calibration procedure 800 may ensure that the position/orientation identification at blocks 808-810 uses sensor data captured at approximately the same time (e.g., within the smallest sampling period), such as by, for example, referencing timestamp information associated with the captured data.

In the example of FIG. 8, the calibration procedure 800 proceeds from block 814 to block 818 when the calibration procedure 800 determines that blocks 808-812 have been executed enough times for the calibration procedure 800 to operate successfully. At block 818, the calibration procedure 800 uses the identified positions/orientations recorded at block 812, in conjunction with the position vector equation 710 and/or orientation vector equation 708 (shown in FIG. 7), to derive/determine the positional/orientational relationship between the helmet tracking system 210 and helmet weld tracking sensor(s) 102 (e.g., position vector 704HW and/or orientation vector 706HW).

In some examples, the identified positions/orientations recorded at block 812 may be used to replace variables in the position vector equation 710 and/or orientation vector equation 708 (shown in FIG. 7). For example, the recorded position(s) of the helmet tracking system 210 relative to the reference point 702 (identified at block 808) may replace the position vector 704RH in the position vector equation 710. As another example, the recorded orientation(s) of the helmet tracking system 210 relative to the reference point 702 (also identified at block 808) may replace the orientation vector 706RH in the position vector equation 710 and/or the position vector equation 710. As another example, the recorded position(s) of the weld tracking sensor(s) 102 relative to the welding-type tool 110 (and/or other trackable object) may replace the position vector 704WT (and/or similar vector) in the position vector equation 710. As another example, the recorded orientation(s) of the weld tracking sensor(s) 102 relative to the welding-type tool 110 (and/or other trackable object) may replace the orientation vector 706WT in the position vector equation 710 and/or the position vector equation 710.

Because the calibration procedure 800 recorded multiple values for each of the above vectors 704/706, replacing the vectors 704/706 with the recorded values may result in several different position vector equations 710 and/or orientation vector equations 708. In some examples, each equation may use coordinated values (e.g., based on time and/or position/orientation synchronized sensor data). Because neither the reference point 702 nor trackable object (i.e., welding-type tool 110 and/or marker(s) 114) are moved during the calibration procedure 800, the position vector(s) 704RT and/or orientation(s) vector 706RT may be treated as (e.g., unknown) constants in the position vector equations 710 and/or orientation vector equations 708. Additionally, because the helmet tracking system 210 and helmet weld tracking sensor(s) 102 were fixed relative to one another at the beginning of the calibration procedure 800, the position vector 704HW and orientation vector 706HW may be assumed to the same across all the position vector equations 710 and/or orientation vector equations 708.

In this way, the (e.g., vector) variables in the position vector equations 710 and/or orientation vector equations 708 may be replaced with known values or (e.g., unknown) constants. In some examples, the calibration procedure 800 may thereby derive/determine the position vector 704HW and orientation vector 706HW from the position vector equations 710 and/or orientation vector equations 708 using various mathematical tools developed for such situations.

In some examples, different position vectors 704HW and/or orientation vectors 706HW may be derived/determined for each different weld tracking sensor 102 (and/or sensor of the helmet tracking system 210). In some examples, the calibration procedure 800 may save the derived/determined position vector 704HW and/or orientation vector 706HW information at block 818 so that the information may be used during the weld tracking process 400 (e.g., at block 408). In the example of FIG. 8, the calibration procedure 800 ends after block 818.

Figure 9:
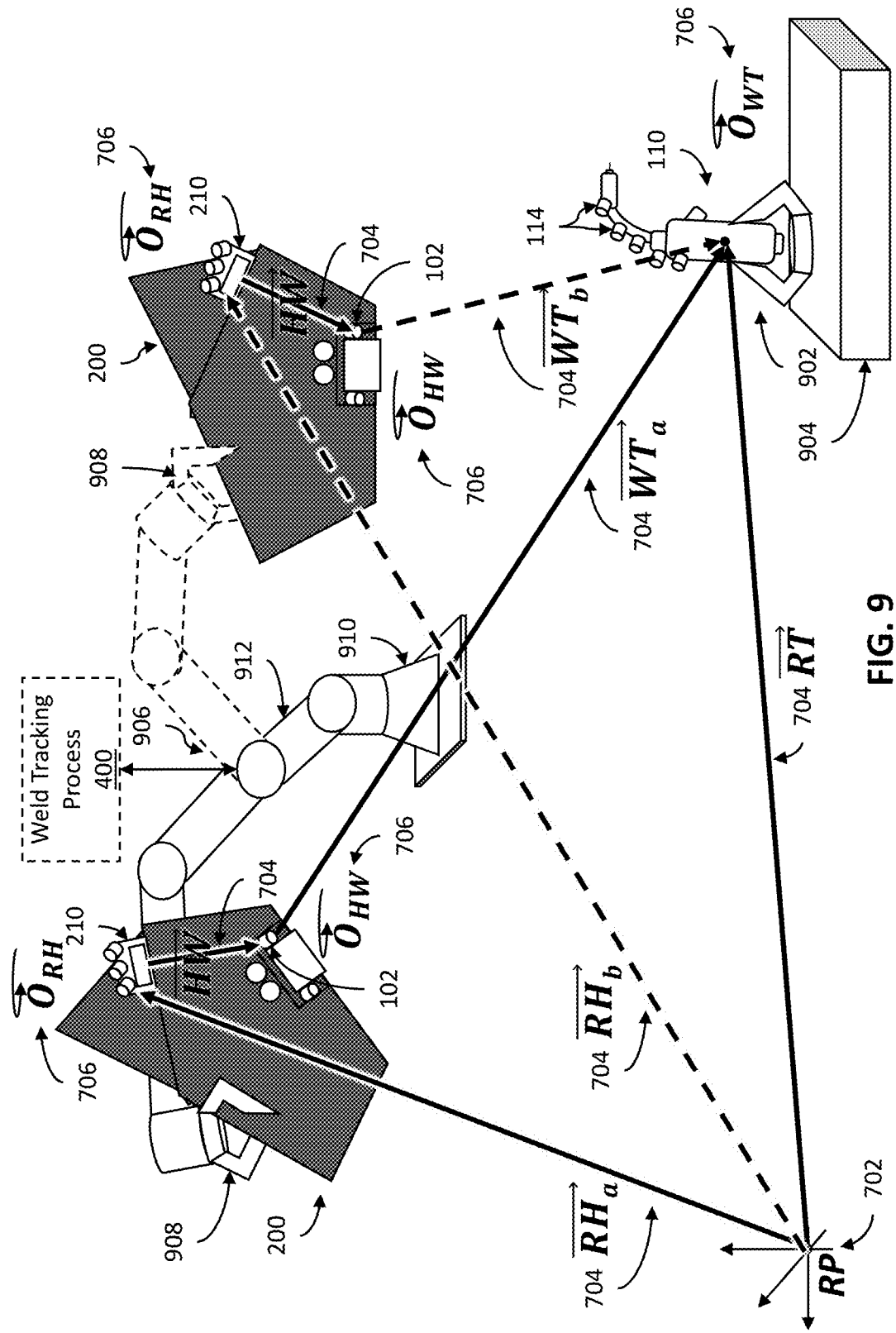
FIG. 9 is a diagram depicting how some of the relationships shown in FIG. 7 might change (or stay the same) during a movement portion of the calibration procedure of FIG. 8, in accordance with aspects of this disclosure.
Figure 10A:
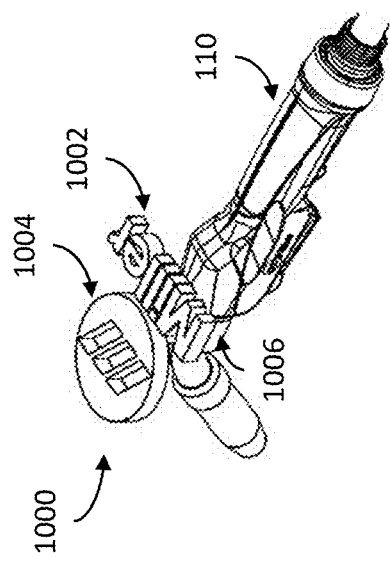
FIGS. 10a-10g show examples of an object that might be used as a visually distinctive marker (e.g., of a welding-type tool), in accordance with aspects of this disclosure.
Figure 10C:
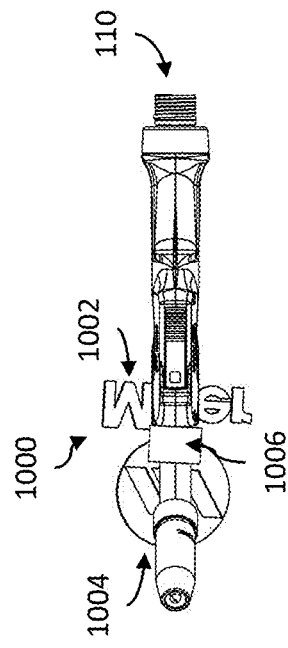
Figure 10B:
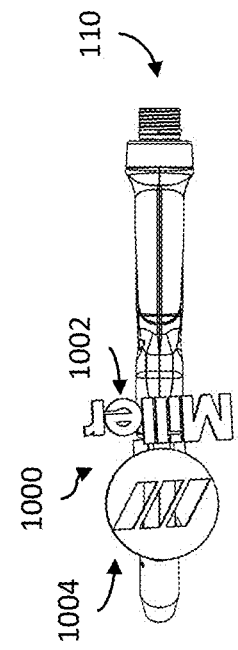
Figure 10D:
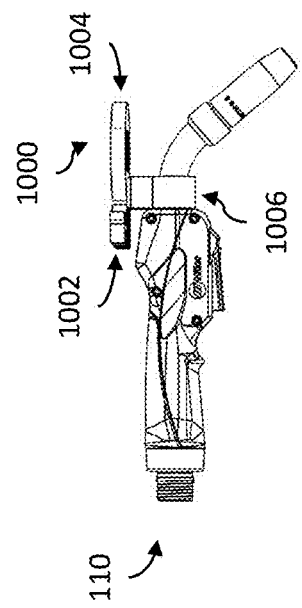
Figure 10E:
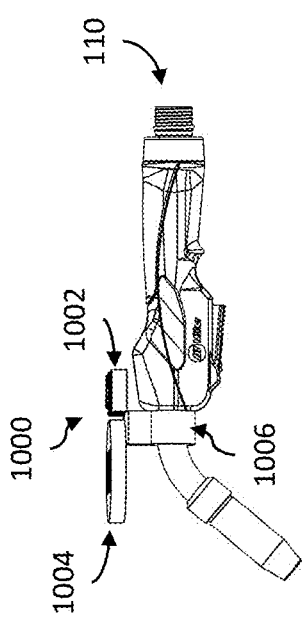
Figure 10F:
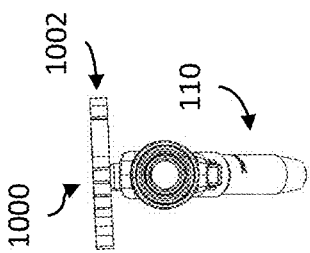
Figure 10G:
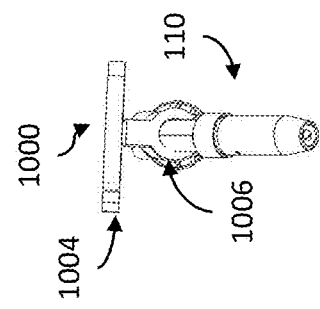

FIG. 9 is a diagram depicting an example of how the position/orientation/vector relationships between the helmet sensor system, reference point 702, and welding-type tool 110 (and/or other trackable object) might change (or not change) after moving the helmet sensor system (e.g., at block 816).

In the example of FIG. 9, the trackable object is the welding-type tool 110 (though a different trackable object may be used in other examples). As shown, the welding-type tool 110 is held in place by a fixture 902 attached to a table 904. The welding-type tool 110 also retains markers 114 to assist with tracking the welding-type tool 110. In some examples, the markers 114 could be used as the trackable object instead of the welding-type tool 110.

In the example of FIG. 9, the helmet tracking system 210 and weld tracking sensor 102 are held in a fixed spatial relationship relative to one another by the welding helmet 200. In some examples, the helmet tracking system 210 and weld tracking sensor 102 may instead be held in a fixed spatial relationship relative to one another by some other mechanism (e.g., a plate, bracket, holder, mount, robot 906, etc.), such as described above. While, in some examples, multiple weld tracking sensors 102 may be part of the welding helmet 200, used in the weld tracking process 400, and/or calibrated via the calibration procedure 800, the example of FIG. 9 focuses on a single weld tracking sensor 102 for the sake of simplicity.

In the example of FIG. 9, a robot 906 grasps the welding helmet 200 via gripper 908. As shown, the robot 906 includes a base 910 connected to a robotic armature 912 having multiple joints and segments. At an end of the armature 912 is a gripper 908 that holds the welding helmet 200. In some examples, the multiple joints and/or segments allow the robotic armature 912 to articulate and/or move with 6 DOF. In some examples, the 6 DOF of the armature 912 allows the robot 906 to move the welding helmet 200 (and associated helmet sensor system) with 6 DOF.

In the example of FIG. 9, the robot 906 moves the welding helmet 200 (and associated helmet sensor system from a first position at the left, to a second position at the right. The movement of the welding helmet 200 involves both a left to right translational movement, and a clockwise rotational movement. Though a single axis movement and single axis rotation is shown in the example of FIG. 9 for the sake of simplicity, in some examples, the robot 906 may move the welding helmet 200 in, and/or rotate the welding helmet 200 about, one, two, or three axes.

In the example of FIG. 9, the robot 906 is in communication with the weld tracking process 400 (and, by extension, the computing system 150 and/or welding helmet 200 executing the weld tracking process 400). In some examples, the robot 906 may move the welding helmet 200 in response to commands from the calibration procedure 800 (e.g., executing as part of the weld tracking process 400). In some examples, the robot 906 may include, or be connected to, a robotic controller configured to control movement of the robot 906. In some examples, the robot 906 may include one or more actuators that induce movement of the robotic armature 912 and/or gripper 908 (e.g., in response to one or more commands from the robotic controller and/or calibration procedure 800). In some examples, the robot 906 may include communication circuitry and/or an associated antenna to enable communication with the weld tracking process 400 (and, by extension, the computing system 150 and/or welding helmet 200).

In the example of FIG. 9, the position vector 704RH (representative of the position of the helmet tracking system 210 relative to the reference point 702) changes after the robot 906 moves the welding helmet 200 from the first position on the left to the second position on the right. This can be seen through the different arrows 704RHa and 704RHb. The orientation vector 706RH (representative of the orientation of the helmet tracking system 210 relative to the reference point 702) also changes after the robot 906 moves the welding helmet 200, as can be inferred from the different orientations of the welding helmet 200 at the first and second positions (given that the reference point 702 does not move).

In the example of FIG. 9, the position vector 704WT (representative of the position of the weld tracking sensor 102 relative to the welding-type tool 110) also changes after the robot 906 moves the welding helmet 200 from the first position on the left to the second position on the right. This can be seen through the different arrows 704WTa and 704WTb. The orientation vector 706WT (representative of the orientation of the weld tracking sensor 102 relative to the welding-type tool 110) also changes after the robot 906 moves the welding helmet 200, as can be inferred from the different orientations of the welding helmet 200 at the first and second positions (given that the welding-type tool 110 is held in place and does not move).

On the other hand, the position vector 704RT (representative of the position of the welding-type tool 110 relative to the reference point 702) does not change after the robot 906 moves the welding helmet 200 from the first position on the left to the second position on the right. Likewise, the orientation vector 706RT (representative of the orientation of the welding-type tool 110 relative to the reference point 702) does not change. This is because the welding-type tool 110 is held in place by the fixture 902, and because the reference point 702 is also stationary.

The position/orientation of the weld tracking sensor 102 relative to the helmet tracking system 210 also does not change after the robot 906 moves the welding helmet 200. This can be inferred from the fact that the helmet tracking system 210 and weld tracking sensors 102 are still shown as retained at the same positions on the welding helmet 200 before and after movement.

While the arrow corresponding to the position vector 704HW (representative of the position of the weld tracking sensor 102 relative to the helmet tracking system 210) appears to change, this is only because the welding helmet 200 has been rotated with respect to our own (real world) perspective. However, from the perspective of the helmet tracking system 210 the position/orientation of the weld tracking sensor 102 would not appear to change because both the weld tracking sensor 102 and helmet tracking system 210 are moved in the same way when the welding helmet 200 is moved. Movement of the welding helmet 200 has no impact on the relative position/orientation of the weld tracking sensor 102 and helmet tracking system 210 retained by the welding helmet 200 (and/or associated vectors 704/706HW), much like movement of planet Earth has no impact on the relative positions/orientations of objects on planet Earth.

While FIG. 9 only depicts one movement of the welding helmet 200 (and associated helmet sensor system), in some examples, there may be many movements during the calibration procedure 800 (e.g., at block 816). In some examples, the calibration procedure 800 may derive/determine the position vector 704HW and orientation vector 706HW using various values recorded during the calibration procedure 800. In some examples, the more times the helmet sensor system is moved (e.g., at block 816), the more precise and/or confident will be the derivations/determinations of the calibration procedure 800. In some examples, the information derived/determined by the calibration procedure 800 may be used to enable the welding helmet 200 to operate as a weld tracking system.

In some examples, the disclosed welding helmet 200 may provide a compact, independent, and/or mobile weld tracking system. This mobile weld tracking system may allow for weld tracking outside of the normally fixed bounds of the weld tracking system 100. In some examples, the welding helmet 200 may track its own position and/or orientation relative to a reference point in a welding environment, as well as the position and/or orientation of a welding-type tool 110 and/or arc 112 relative to the helmet. In this way, the welding helmet 200 can differentiate between movement of the welding helmet 200 and movement of the tool 110 and/or arc 112. By tracking movement of the tool 110 and/or arc 112 the weld tracking system can analyze the welding technique of an operator 104, as well as weld quality, welding location, and/or weld sequence. In cases where the weld tracking data, welding technique, weld quality, welding location, and/or weld sequence deviates from what is expected, the welding helmet 200 may offer corrective feedback, change welding parameters to compensate, and/or disable welding-type operations entirely. In some examples, the weld tracking system 100 and/or welding helmet 200 may be calibrated using the welding-type tool 110 (and/or calibration tool 132) to provide more robust performance.

The present methods and/or systems may be realized in hardware, software, or a combination of hardware and software. The present methods and/or systems may be realized in a centralized fashion in at least one computing system, or in a distributed fashion where different elements are spread across several interconnected computing or cloud systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

As used herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

As utilized herein, the terms "e.g.," and "for example" set off lists of one or more non-limiting examples, instances, or illustrations.

As used herein, the terms "coupled," "coupled to," and "coupled with," each mean a structural and/or electrical connection, whether attached, affixed, connected, joined, fastened, linked, and/or otherwise secured. As used herein, the term "attach" means to affix, couple, connect, join, fasten, link, and/or otherwise secure. As used herein, the term "connect" means to attach, affix, couple, join, fasten, link, and/or otherwise secure.

As used herein the terms "circuits" and "circuitry" refer to physical electronic components (i.e., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, circuitry is "operable" and/or "configured" to perform a function whenever the circuitry comprises the necessary hardware and/or code (if any is necessary) to perform the function, regardless of whether performance of the function is disabled or enabled (e.g., by a user-configurable setting, factory trim, etc.).

As used herein, a control circuit may include digital and/or analog circuitry, discrete and/or integrated circuitry, microprocessors, DSPs, etc., software, hardware and/or firmware, located on one or more boards, that form part or all of a controller, and/or are used to control a welding process, and/or a device such as a power source or wire feeder.

As used herein, the term "processor" means processing devices, apparatus, programs, circuits, components, systems, and subsystems, whether implemented in hardware, tangibly embodied software, or both, and whether or not it is programmable. The term "processor" as used herein includes, but is not limited to, one or more computing devices, hardwired circuits, signal-modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities, and combinations of any of the foregoing. The processor may be, for example, any type of general purpose microprocessor or microcontroller, a digital signal processing (DSP) processor, an application-specific integrated circuit (ASIC), a graphic processing unit (GPU), a reduced instruction set computer (RISC) processor with an advanced RISC machine (ARM) core, etc. The processor may be coupled to, and/or integrated with a memory device.

As used, herein, the term "memory" and/or "memory device" means computer hardware or circuitry to store information for use by a processor and/or other digital device. The memory and/or memory device can be any suitable type of computer memory or any other type of electronic storage medium, such as, for example, read-only memory (ROM), random access memory (RAM), cache memory, compact disc read-only memory (CDROM), electro-optical memory, magneto-optical memory, programmable read-only memory (PROM), erasable programmable read-only memory (EPROM), electrically-erasable programmable read-only memory (EEPROM), a computer-readable medium, or the like. Memory can include, for example, a non-transitory memory, a non-transitory processor readable medium, a non-transitory computer readable medium, non-volatile memory, dynamic RAM (DRAM), volatile memory, ferroelectric RAM (FRAM), first-in-first-out (FIFO) memory, last-in-first-out (LIFO) memory, stack memory, non-volatile RAM (NVRAM), static RAM (SRAM), a cache, a buffer, a semiconductor memory, a magnetic memory, an optical memory, a flash memory, a flash card, a compact flash card, memory cards, secure digital memory cards, a microcard, a minicard, an expansion card, a smart card, a memory stick, a multimedia card, a picture card, flash storage, a subscriber identity module (SIM) card, a hard drive (HDD), a solid state drive (SSD), etc. The memory can be configured to store code, instructions, applications, software, firmware and/or data, and may be external, internal, or both with respect to the processor.

The term "power" is used throughout this specification for convenience, but also includes related measures such as energy, current, voltage, and enthalpy. For example, controlling "power" may involve controlling voltage, current, energy, and/or enthalpy, and/or controlling based on "power" may involve controlling based on voltage, current, energy, and/or enthalpy.

As used herein, welding-type refers to welding (including laser welding and/or hot wire welding), cladding (including laser cladding), brazing, plasma cutting, induction heating, carbon arc cutting or gouging, hot wire preheating, and/or resistive preheating.

As used herein, a welding-type tool refers to a tool suitable for and/or capable of welding (including laser welding and/or hot wire welding), cladding (including laser cladding), brazing, plasma cutting, induction heating, carbon arc cutting or gouging, hot wire preheating, and/or resistive preheating.

As used herein, welding-type power refers to power suitable for welding (including laser welding and/or hot wire welding), cladding (including laser cladding), brazing, plasma cutting, induction heating, carbon arc cutting or gouging, hot wire preheating, and/or resistive preheating.

As used herein, a welding-type power supply and/or welding-type power source refers to a device capable of, when input power is applied thereto, supplying output power suitable for welding (including laser welding and/or hot wire welding), cladding (including laser cladding), brazing, plasma cutting, induction heating, carbon arc cutting or gouging, hot wire preheating, and/or resistive preheating; including but not limited to transformer-rectifiers, inverters, converters, resonant power supplies, quasi-resonant power supplies, switch-mode power supplies, etc., as well as control circuitry and other ancillary circuitry associated therewith.

As used herein, disable may mean deactivate, incapacitate, and/or make inoperative. As used herein, enable may mean activate and/or make operational.

Disabling of circuitry, actuators, and/or other hardware may be done via hardware, software (including firmware), or a combination of hardware and software, and may include physical disconnection, de-energization, and/or a software control that restricts commands from being implemented to activate the circuitry, actuators, and/or other hardware. Similarly, enabling of circuitry, actuators, and/or other hardware may be done via hardware, software (including firmware), or a combination of hardware and software, using the same mechanisms used for disabling.

What is claimed is:

1. A non-transitory computer readable medium comprising machine readable instructions which, when executed by a processor, cause the processor to:
    identify an initial first position of a first sensor system relative to a reference point based on initial first sensor data captured by the first sensor system;
    identify an initial second position of a second sensor system relative to a stationary trackable object based on initial second sensor data captured by the second sensor system, the first sensor system being in a fixed spatial relationship relative to the second sensor system, the first and second sensor systems comprising a helmet sensor system;
    determine, after a first duration of movement of the helmet sensor system, a subsequent first position of the first sensor system relative to the reference point based on subsequent first sensor data captured by the first sensor system,
    determine, after the first duration of movement of the helmet sensor system, a subsequent second position of the second sensor system relative to the trackable object based on subsequent second sensor data captured by the second sensor system; and
    identify a vector relationship between the first sensor system and the second sensor system based on the initial first position of the first sensor system, the initial second position of the second sensor system, the subsequent first position of the first sensor system, and the subsequent second position of the second sensor system.

2. The non-transitory computer readable medium of claim 1, wherein the subsequent first sensor data and subsequent second sensor data are captured at approximately the same time, or captured when the helmet sensor system is stationary.

3. The non-transitory computer readable medium of claim 1, further comprising machine readable instructions which, when executed by the processor, cause the processor to record the vector relationship in the non-transitory computer readable medium or a separate memory.

4. The non-transitory computer readable medium of claim 1, wherein the trackable object is a welding-type tool, a marker, or a rigid body configuration of markers.

5. The non-transitory computer readable medium of claim 1, further comprising machine readable instructions which, when executed by the processor, cause the processor to:
    identify an initial first orientation of the first sensor system relative to the reference point based on the initial first sensor data captured by the first sensor system;
    identify an initial second orientation of the second sensor system relative to the stationary trackable object based on the initial second sensor data captured by the second sensor system;
    determine, after the first duration of movement of the helmet sensor system, a subsequent first orientation of the first sensor system relative to the reference point based on the subsequent first sensor data captured by the first sensor system; and
    determine, after the first duration of movement of the helmet sensor system, a subsequent second orientation of the second sensor system relative to the trackable object based on the subsequent second sensor data captured by the second sensor system,
    wherein the vector relationship between the first sensor system and the second sensor system is further identified based on the initial first orientation of the first sensor system, the initial second orientation of the second sensor system, the subsequent first orientation of the first sensor system, and the subsequent second orientation of the second sensor system.

6. The non-transitory computer readable medium of claim 1, further comprising machine readable instructions which, when executed by the processor, cause the processor to:

capture, after, or between, a plurality of additional movements of the helmet sensor system, additional first sensor data and additional second sensor data via the first sensor system and second sensor system, respectively;

determine additional first positions of the first sensor system relative to the reference point based on the additional first sensor data captured by the first sensor system; and determine additional second positions of the second sensor system relative to the trackable object based on the additional second sensor data captured by the second sensor system, wherein the vector relationship between the first sensor system and the second sensor system is further determined based on the additional first positions of the first sensor system, and the additional second positions of the second sensor system.

7. The non-transitory computer readable medium of claim 1, further comprising machine readable instructions which, when executed by the processor, cause the processor to:

monitor, via the first sensor system, when the first sensor system is retained by a welding helmet, a helmet position and a helmet orientation of the welding helmet relative to a second reference point in a welding environment;

track, via the second sensor system, when the second sensor system is retained by the welding helmet, a position or orientation of the welding-type tool, or of an arc produced by the welding-type tool, relative to the second sensor system; and determine a welding position or welding orientation of the welding-type tool, or the arc, relative to the reference point based on the helmet position and the helmet orientation relative to the reference point, the position or orientation of the welding-type tool, or the arc, relative to the second sensor system, and the vector relationship between the first sensor system and second sensor system.

8. A method of determining a vector relationship between a first sensor system and a second sensor system of a welding helmet, the method comprising:

determining, via processing circuitry, an initial first position and an initial first orientation of a first sensor system relative to a reference point based on initial first sensor data captured by the first sensor system;

determining, via the processing circuitry, an initial second position and an initial second orientation of a second sensor system relative to a stationary trackable object based on initial second sensor data captured by the second sensor system, the first sensor system being in a fixed spatial relationship relative to the second sensor system, the first and second sensor systems comprising a helmet sensor system;

after a first duration of movement of the helmet sensor system, determining, via the processing circuitry, a subsequent first position and a subsequent first orientation of the first sensor system relative to the reference point based on subsequent first sensor data captured by the first sensor system, after the first duration of movement of the helmet sensor system, determining, via the processing circuitry, a subsequent second position and a subsequent second orientation of the second sensor system relative to the trackable object based on subsequent second sensor data captured by the second sensor system; and determining, via the processing circuitry, the vector relationship between the first sensor system and the second sensor system based on the initial first position of the first sensor system, the initial first orientation of the first sensor system, the initial second position of the second sensor system, the initial second orientation of the second sensor system, the subsequent first position of the first sensor system, the subsequent first orientation of the first sensor system, the subsequent second position of the second sensor system, and the subsequent second orientation of the second sensor system.

9. The method of claim 8, further comprising executing the first duration of movement of the helmet sensor system via a movement system.

10. The method of claim 8, wherein the first duration of movement is executed while keeping the trackable object in a field of view of the second sensor system.

11. The method of 8, further comprising recording the vector relationship in memory circuitry of the welding helmet, wherein the vector relationship is associated with a timestamp when recorded in memory circuitry.

12. The method of claim 8, wherein the trackable object is a welding-type tool, a marker, or a rigid body configuration of markers.

13. The method of claim 8, further comprising:

after, or between, a plurality of additional movements of the helmet sensor system, capturing additional first sensor data and additional second sensor data via the first sensor system and second sensor system, respectively;

determining, via the processing circuitry, additional first positions and additional first orientations of the first sensor system relative to the reference point based on the additional first sensor data captured by the first sensor system; and determining, via the processing circuitry, additional second positions and additional second orientations of the second sensor system relative to the trackable object based on the additional second sensor data captured by the second sensor system, wherein the vector relationship between the first sensor system and the second sensor system is further determined based on the additional first positions and additional first orientations of the first sensor system, and the additional second positions and additional second orientations of the second sensor system.

14. The method of claim 8, further comprising:

monitoring, via the first sensor system when the helmet sensor system is retained by the welding helmet, a helmet position and a helmet orientation of the welding helmet relative to a second reference point in a welding environment;

tracking, via the second sensor system, a position or orientation of the welding-type tool, or of an arc produced by the welding-type tool, relative to the second sensor system; and determining, via control circuitry of the welding helmet, a welding position or welding orientation of the welding-type tool, or the arc, relative to the reference point based on the helmet position and the helmet orientation relative to the reference point, the position or orientation of the welding-type tool, or the arc, relative to the second sensor system, and the vector relationship between the first sensor system and second sensor system.

15. A welding system, comprising:
a helmet sensor system comprising a first sensor system and a second sensor system, the first sensor system being in a fixed spatial relationship relative to the second sensor system;
processing circuitry; and
memory circuitry comprising machine readable instructions which, when executed by the processing circuitry, cause the processing circuitry to:
   identify an initial first position of the first sensor system relative to a reference point based on initial first sensor data captured by the first sensor system,
   identify an initial second position of the second sensor system relative to a stationary trackable object based on initial second sensor data captured by the second sensor system,
   determine, after a first duration of movement of the helmet sensor system, a subsequent first position of the first sensor system relative to the reference point based on subsequent first sensor data captured by the first sensor system,
   determine, after the first duration of movement of the helmet sensor system, a subsequent second position of the second sensor system relative to the trackable object based on subsequent second sensor data captured by the second sensor system, and
   identify a vector relationship between the first sensor system and the second sensor system based on the initial first position of the first sensor system, the initial second position of the second sensor system, the subsequent first position of the first sensor system, and the subsequent second position of the second sensor system.

16. The welding system of claim 15, wherein the fixed spatial relationship is identical to a fixed helmet relationship between the first sensor system and second sensor system when the first sensor system and second system are retained by a welding helmet.

17. The welding system of claim 15, further comprising the trackable object, the trackable object comprising a welding-type tool or a rigid body configuration of markers.

18. The welding system of claim 15, the memory circuitry further comprising machine readable instructions which, when executed by the processor, cause the processor to:
   identify an initial first orientation of the first sensor system relative to the reference point based on the initial first sensor data captured by the first sensor system;
   identify an initial second orientation of the second sensor system relative to the stationary trackable object based on the initial second sensor data captured by the second sensor system;
   determine, after the first duration of movement of the helmet sensor system, a subsequent first orientation of the first sensor system relative to the reference point based on the subsequent first sensor data captured by the first sensor system; and
   determine, after the first duration of movement of the helmet sensor system, a subsequent second orientation of the second sensor system relative to the trackable object based on the subsequent second sensor data captured by the second sensor system,
   wherein the vector relationship between the first sensor system and the second sensor system is further identified based on the initial first orientation of the first sensor system, the initial second orientation of the second sensor system, the subsequent first orientation of the first sensor system, and the subsequent second orientation of the second sensor system.

19. The welding system of claim 15, the memory circuitry further comprising machine readable instructions which, when executed by the processor, cause the processor to:
   capture, after, or between, a plurality of additional movements of the helmet sensor system, additional first sensor data and additional second sensor data via the first sensor system and second sensor system, respectively;
   determine additional first positions of the first sensor system relative to the reference point based on the additional first sensor data captured by the first sensor system; and
   determine additional second positions of the second sensor system relative to the trackable object based on the additional second sensor data captured by the second sensor system,
   wherein the vector relationship between the first sensor system and the second sensor system is further determined based on the additional first positions of the first sensor system, and the additional second positions of the second sensor system.

20. The welding system of claim 15, the memory circuitry further comprising machine readable instructions which, when executed by the processor, cause the processor to:
   monitor, via the first sensor system when the first sensor system is retained by the welding helmet, a helmet position and a helmet orientation of the welding helmet relative to a second reference point in a welding environment;
   track, via the second sensor system when the second sensor system is retained by the welding helmet, a position or orientation of the welding-type tool, or of an arc produced by the welding-type tool, relative to the second sensor system; and
   determine a welding position or welding orientation of the welding-type tool or the arc, relative to the reference point, based on the helmet position and the helmet orientation relative to the reference point, the position or orientation of the welding-type tool or arc relative to the second sensor system, and the vector relationship between the first sensor system and second sensor system.

* * * * *